US011198714B2

(12) United States Patent
Drenser et al.

(10) Patent No.: US 11,198,714 B2
(45) **Date of Patent: *Dec. 14, 2021**

(54) SYNTHETIC TRUNCATED NORRIN PROTEIN

(71) Applicant: Retinal Solutions, LLC, Rochester, MI (US)

(72) Inventors: Kimberly Drenser, Rochester, MI (US); Michael T. Trese, Rochester, MI (US); Antonio Capone, Rochester, MI (US)

(73) Assignee: RETINAL SOLUTIONS LLC, Rochester, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/829,283

(22) Filed: Mar. 25, 2020

(65) Prior Publication Data

US 2020/0299344 A1 Sep. 24, 2020

Related U.S. Application Data

(63) Continuation of application No. 16/214,225, filed on Dec. 10, 2018, now Pat. No. 10,669,321, and a continuation-in-part of application No. 14/733,876, filed on Jun. 8, 2015, now Pat. No. 10,206,978.

(60) Provisional application No. 62/596,349, filed on Dec. 8, 2017.

(51) Int. Cl.

| | |
|---|---|
| *C07K 14/515* | (2006.01) |
| *A61K 38/18* | (2006.01) |
| *C07K 14/47* | (2006.01) |
| *C07K 14/475* | (2006.01) |
| *A61P 27/02* | (2006.01) |
| *A61K 38/00* | (2006.01) |
| *A61K 9/00* | (2006.01) |

(52) U.S. Cl.
CPC ...... *C07K 14/4705* (2013.01); *A61K 38/1891* (2013.01); *C07K 14/475* (2013.01); *A61K 9/0048* (2013.01); *A61K 9/0051* (2013.01); *A61K 38/00* (2013.01); *A61P 27/02* (2018.01); *C07K 14/515* (2013.01)

(58) Field of Classification Search
CPC . C07K 14/475; C07K 14/4705; C07K 14/515
See application file for complete search history.

(56) References Cited

U.S. PATENT DOCUMENTS

| | | | | |
|---|---|---|---|---|
| 4,588,585 | A | 5/1986 | Mark et al. | |
| 5,378,475 | A | 1/1995 | Smith et al. | |
| 5,773,019 | A | 6/1998 | Ashton et al. | |
| 6,001,386 | A | 12/1999 | Ashton et al. | |
| 6,217,895 | B1 | 4/2001 | Guo et al. | |
| 6,375,972 | B1 | 4/2002 | Guo et al. | |
| 6,756,058 | B2 | 6/2004 | Brubaker et al. | |
| 9,114,078 | B2 | 8/2015 | Drenser | |
| 10,206,978 | B2 * | 2/2019 | Trese | A61P 29/00 |
| 10,669,321 | B2 * | 6/2020 | Drenser | A61P 27/02 |
| 2004/0054374 | A1 | 3/2004 | Weber et al. | |
| 2005/0281861 | A1 | 12/2005 | Hughes et al. | |
| 2010/0129375 | A1 | 5/2010 | Junge et al. | |
| 2010/0239499 | A1 | 9/2010 | Drenser | |
| 2014/0171356 | A1 | 6/2014 | Habib et al. | |
| 2015/0376252 | A1 * | 12/2015 | Xu | A61K 45/06 514/7.6 |

FOREIGN PATENT DOCUMENTS

| | | |
|---|---|---|
| JP | 2003524381 A | 8/2003 |
| WO | 2009114878 A2 | 9/2009 |
| WO | 2014130728 A1 | 8/2014 |
| WO | 2014143022 A1 | 9/2014 |

OTHER PUBLICATIONS

Mark, D.F. et al., "Site-specific mutagenesis of the human fibroblast interferon gene", Proceedings of the National Academy of Sciences, Sep. 1984, pp. 5662-5666, vol. 81.
Meindl, A. et al., "Norrie disease is caused by mutations in an extracellular protein resembling C-terminal globular domain of mucins", Nature Genetics, Oct. 1992, pp. 139-143, vol. 2, © 1992 Nature Publishing Group.
Berger, W. et al., "Mutations in the candidate gene for Norrie disease", Human Molecular Genetics, 1992, pp. 461-465, vol. 1, No. 7, © Oxford University Press.
Chen, Z-Y. et al., "A mutation in the Norrie disease gene (NDP) associated with X-linked familial exudative vitreoretinopathy", Nature Genetics, Oct. 1993, pp. 180-183, vol. 5, © 1993 Nature Publishing Group.
Mcdonald, N.Q. et al., "A Structural Superfamily of Growth Factors Containing a Cystine Knot Motif", Cell, May 7, 1993, pp. 421-424, vol. 73, © 1993 by Cell Press.
Meitinger, T. et al., "Molecular Modeling of the Norrie Disease Protein Predicts a Cystine Knot Growth Factor Tertiary Structure", Nature Genetics, Dec. 1993, pp. 376-380, vol. 5.
Black, G. et al., "The Molecular Biology of Norrie's Disease", Eye, 1994, pp. 491-496, vol. 8, © 1994 Royal College of Ophthalmologists.
Schuback, D.E. et al., "Mutations in the Norrie Disease Gene", Human Mutation, 1995, pp. 285-292, vol. 5, © 1995 Wiley-Liss, Inc.
Shastry, B.S. et al., "Linkage and Candidate Gene Analysis of X-Linked Familial Exudative Vitreoretinopathy", Genomics, 1995, pp. 341-344, vol. 27, © 1995 by Academic Press, Inc.

(Continued)

*Primary Examiner* — Zachary C Howard
(74) *Attorney, Agent, or Firm* — Blue Filament Law PLLC

(57) ABSTRACT

A synthetic truncated norrin protein is provided. The synthetic truncated norrin protein is a −24 residue N-terminus norrin truncate relative to SEQ ID. NO. 1 that retains the cysteine-knot motif and frizzled-4 binding properties and has a mutation in the cysteine-knot motif in at least one position 81-90 of SEQ ID. NO. 1 that interferes with protease cleavage of the resulting protein thereby extending the biological half-life thereof in vivo relative to native norrin.

10 Claims, 10 Drawing Sheets
(4 of 10 Drawing Sheet(s) Filed in Color)

Specification includes a Sequence Listing.

(56) References Cited

OTHER PUBLICATIONS

Berger, W. et al., "An animal model for Norrie disease (ND): gene targeting of the mouse ND gene", Human Molecular Genetics, 1996, pp. 51-59, vol. 5, No. 1, © 1996 Oxford University Press.
Perez-Vilar, J. et al., "Norrie Disease Protein (Norrin) Forms Disulfide-linked Oligomers Associated with the Extracellular Matrix", The Journal of Biological Chemistry, Dec. 26, 1997, pp. 33410-33415, vol. 272, No. 52, © 1997 by The American Society for Biochemistry and Molecular Biology, Inc.
Willert, K. et al., "β-catenin: a key mediator of Wnt signaling", Current Opinion in Genetics & Development, 1998, pp. 95-102, vol. 8, © Current Biology Ltd.
Berger, W., "Molecular Dissection of Norrie Disease", Acta Anatomica, 1998, pp. 95-100, vol. 162, © 1998 S. Karger AG.
Black, G.C.M. et al., "Coats' disease of the retina (unilateral retinal telangiectasis) caused by somatic mutation in the NDP gene: a role for norrin in retinal angiogenesis", Human Molecular Genetics, 1999, pp. 2031-2035, vol. 8, No. 11, © 1999 Oxford University Press.
Talks, S. J. et al., "De novo mutations in the 5' regulatory region of the Norrie disease gene in retinopathy of prematurity", Journal of Medical Genetics, 2001, pp. 1-6, vol. 38:e46.
Hiraoka, M. et al., "Insertion and deletion mutations in the dinucleotide repeat region of the Norrie disease gene in patients with advanced retinopathy of prematurity", Journal of Human Genetics, 2001, pp. 178-181, vol. 46, © 2001 Jpn Soc Hum Genet and Springer-Verlag.
Robitaille, J. et al., "Mutant frizzled-4 disrupts retinal angiogenesis in familial exudative vitreoretinopathy", Nature Genetics, Sep. 2002 (Published online: Aug. 12, 2002), pp. 326-330, vol. 32, © 2002 Nature Publishing Group; DOI: 10.1038/ng957.
Fu, K. et al., "A Potential Approach for Decreasing the Burst Effect of Protein from PLGA Microspheres", Journal of Pharmaceutical Sciences, Aug. 2003, pp. 1582-1591, vol. 92, No. 8, © 2003 Wiley-Liss, Inc. and the American Pharmacists Association.
Xu, Q. et al., "Vascular Development in the Retina and Inner Ear: Control by Norrin and Frizzled-4, a High-Affinity Ligand-Receptor Pair", Cell, Mar. 19, 2004, pp. 883-895, vol. 116, © 2004 by Cell Press.
Clevers, H., "Wnt Signaling: Ig-Norrin the Dogma", Current Biology, Jun. 8, 2004, pp. R436-R437, vol. 14, © 2004 Elsevier Ltd.; DOI: 10.1016/j.cub.2004.05.039.
Niehrs, C., "Norrin and Frizzled: A New Vein for the Eye", Developmental Cell, Apr. 2004, pp. 453-461, vol. 6, © 2004 by Cell Press.
Yao, R. et al., "MAGI-3 is involved in the regulation of the JNK signaling pathway as a scaffold protein for frizzled and Ltap", Oncogene, 2004, pp. 6023-6030, vol. 23, © 2004 Nature Publishing Group; DOI: 10.1038/sj.onc.1207817.
Hutcheson, K.A. et al., "Norrie disease gene sequence variants in an ethnically diverse population with retinopathy of prematurity", Molecular Vision, Jul. 14, 2005, pp. 501-508, vol. 11, ©0 2005 Molecular Vision.
Hines, L. et al., "Norrie disease pseudoglioma protein, partial [synthetic construct]", NCBI, 2005, 2 pages, GenBank accession No. AAX29917.1.
Gavard, J. et al., "VEGF controls endothelial-cell permeability by promoting the β-arrestin-dependent endocytosis of VE-cadherin", Nature Cell Biology, Nov. 2006, pp. 1223-1234, vol. 8, No. 11, © 2006 Nature Publishing Group; DOI: 10.1038/ncb1486.
Groten, T. et al., "Cell junctional proteins in the human corpus luteum: changes during the normal cycle and after HCG treatment", Human Reproduction, 2006 (Advance Access publication Aug. 21, 2006), pp. 3096-3102, vol. 21, No. 12, © 2006 The Authors; DOI: 10.1093/humrep/del286.
Smallwood, P.M. et al., "Mutational Analysis of Norrin-Frizzled4 Recognition", The Journal of Biological Chemistry, Feb. 9, 2007, pp. 4057-4068, vol. 282, No. 6, © 2007 The American Society for Biochemistry and Molecular Biology, Inc.
Jiang, C. et al., "Intravitreal injections of GDNF-loaded biodegradable microspheres are neuroprotective in a rat model of glaucoma", Molecular Vision, Sep. 24, 2007, pp. 1783-1792, vol. 13, © 2007 Molecular Vision.
Taddei, A. et al., "Endothelial adherens junctions control tight junctions by VE-cadherin-mediated upregulation of claudin-5", Nature Cell Biology, Aug. 2008, pp. 923-934, vol. 10, No. 8, © 2008 Macmillan Publishers Limited; DOI: 10.1038/ncb1752.
Schulzke, J. D. et al., "Epithelial Tight Junctions in Intestinal Inflammation", Molecular Structure and Function of the Tight Junction: Ann. N.Y. Acad. Sci., May 2009, pp. 294-300, vol. 1165, © 2009 New York Academy of Sciences; DOI: 10.1111/j.1749-6632.2009.04062.x.
Ye, X. et al., "Norrin, Frizzled4, and Lrp5 signaling in endothelial cells controls a genetic program for retinal vascularization", Cell, Author Manuscript available in PMC Apr. 16, 2010, Published in final edited form on Oct. 16, 2009, pp. 285-298, vol. 139, No. 2; DOI: 10.1016/j.cell.2009.07.047.
Junge, H.J. et al., "TSPAN12 Regulates Retinal Vascular Development by Promoting Norrin- but Not Wnt-Induced FZD4/β-Catenin Signaling", Cell, Oct. 16, 2009, pp. 299-311, vol. 139, © 2009 Elsevier Inc; DOI: 10.1016/j.cell.2009.07.048.
Ohlmann, A. et al., "Norrin Promotes Vascular Regrowth after Oxygen-Induced Retinal Vessel Loss and Suppresses Retinopathy in Mice", Neurobiology of Disease, Jan. 6, 2010, pp. 183-193, vol. 30, No. 1, © 2010 the Authors; DOI: 10.1523/JNEUROSCI.3210-09.2010.
Chakraborty, S. et al., "Lymphatic system acts as a vital link between metabolic syndrome and inflammation", Ann. N.Y. Acad. Sci., Author Manuscript available in PMC Oct. 1, 2011, Published in final edited form in Oct. 2010, pp. E94-102, vol. 1207 (Suppl. 1); DOI: 10.1111/j.1749-6632.2010.05752.x.
National Eye Institute, Definition of Macular Edema, Apr. 5, 2010, 2 pages; https://www.nei.nih.gov/faqs/retina-macular-edema.
Paes, K.T. et al., "Frizzled 4 Is Required for Retinal Angiogenesis and Maintenance of the Blood-Retina Barrier", Investigative Ophthalmology & Visual Science, Aug. 2011, pp. 6452-6461, vol. 52, No. 9, © 2011 The Association for Research in Vision and Ophthalmology, Inc.
Descamps, B. et al., "Frizzled 4 Regulates Arterial Network Organization Through Noncanonical Wnt/Planar Cell Polarity Signaling", Circulation Research, Jan. 6, 2012, 30 pages, vol. 110, © 2011 American Heart Association, Inc.; DOI: 10.1161/CIRCRESAHA.111.250936.
Ohlmann, A. et al., "Norrin: Molecular and functional properties of an angiogenic and neuroprotective growth factor". Progress in Retinal and Eye Research, 2012, pp. 243-257, vol. 31, © 2012 Elsevier Ltd.I DOI: 10.1016/j.preteyeres.2012.02.002.
Luissint, A-C. et al., "Tight junctions at the blood brain barrier: physiological architecture and disease-associated dysregulation", Fluids and Barriers of the CNS, 2012, pp. 1-12, vol. 9, No. 23, © 2012 Luissint et al.
Wang, Y. et al., "Norrin/Frizzled4 Signaling in Retinal Vascular Development and Blood Brain Barrier Plasticity", Cell, Dec. 7, 2012, pp. 1332-1344, vol. 151, © 2012 Elsevier Inc; DOI: 10.1016/j.cell.2012.10.042.
Koo, N.K. et al., "Resolution of Macular Edema after Systemic Treatment with Furosemide", Korean J. Ophthalmol., 2012, pp. 312-315, vol. 26, No. 4, © 2012 The Korean Ophthalmological Society; DOI: 10.3341/kjo.2012.26.4.312.
Romero-Aroca, P., "Current status in diabetic macular edema treatments", World Journal of Diabetes, Oct. 15, 2013, pp. 165-169, vol. 4, No. 5, © 2013 Baishideng; DOI: 10.4239/wjd.v4.i5.165.
Ke, J. et al., "Structure and function of Norrin in assembly and activation of a Frizzled 4—Lrp5/6 complex", Genes and Development, 2013, pp. 2305-2319, vol. 27, © 2013 Cold Spring Harbor Laboratory Press; DOI: 10.1101/gad.228544.113.
Lee, H. et al., "Norrin expression in endothelial cells in the developing mouse retina", Acta Histochemica, 2013, pp. 447-451, vol. 115, © 2012 Elsevier GmbH; DOI: 10.1016/j.acthis.2012.10.008.
Weidemann, A.K. et al., "Vascular endothelial growth factor inhibitors: investigational therapies for the treatment of psoriasis", Clini-

(56) References Cited

OTHER PUBLICATIONS cal, Cosmetic and Investigational Dermatology, Sep. 25, 2013, pp. 233-244, vol. 6, © 2013 Weidmann et al.; DOI: 10.2147/CCID.S35312.
Braunger, B.M. et al., "Constitutive overexpression of Norrin activates Wnt/β-catenin and endothelin-2 signaling to protect photoreceptors from light damage", Neurobiology of Disease, 2013, pp. 1-12, vol. 50, © 2012 Elsevier Inc.; DOI: 10.1016/j.nbd.2012.09.008.
Planutis, K. et al., "A novel signaling pathway regulates colon cancer angiogenesis through Norrin", Scientific Reports, Jul. 9, 2014, pp. 1-5, vol. 4, No. 5630, DOI: 10.1038/srep05630.
Zhou, Y. et al., "Canonical WNT signaling components in vascular development and barrier formation", The Journal of Clinical Investigation, Sep. 2014, pp. 3825-3846, vol. 124, No. 9, DOI: 10.1172/JCI76431.
Daily, W. et al., "Norrin Increases Vessel Integrity upon VEGF Induced Permeability", ARVO Annual Meeting Abstract, Investigative Ophthalmology & Visual Science, Apr. 2014, p. 5400, vol. 55, No. 13, © 2014 The Association for Research in Vision and Ophthalmology, Inc.
Tang, M. et al., "norrin precursor [*Homo sapiens*]", NCBI, 2014, 3 pages, GenBank accession No. NP_000257.1.
Chen, Y. et al., "Norrin protected Blood Brain Barrier via Frizzled 4/β-catenin Pathway after Subarachnoid Hemorrhage in Rats", Stroke, Author manuscript available in PMC Feb. 1, 2016, Published in final edited form Feb. 2015, pp. 529-536, vol. 46, No. 2; DOI: 10.1161/STROKEAHA.114.007265.
Chen, Y. et al., "Response to Letter regarding Article, Norrin Protected Blood-Brain Barrier via Frizzled-4/β-catenin Pathway after Subarachnoid Hemorrhage in Rats", Stroke, Author manuscript available in PMC Apr. 1, 2016, Published in final edited form Apr. 2015, 2 pages, vol. 46(4): e91; DOI: 10.1161/STROKEAHA.115.008779.
International Search Report dated Sep. 9, 2016 for International Application No. PCT/US2016/036402 filed Jun. 8, 2016.
International Search Report dated Sep. 12, 2016 for International Application No. PCT/US2016/036438 filed Jun. 8, 2016.
Supplementary European Search Report dated Dec. 19, 2018 for European Application No. 16808183 filed Jun. 8, 2016.
U.S. Appl. No. 16/214,225, filed Dec. 10, 2018, Pending.
U.S. Appl. No. 14/733,876, filed Jun. 8, 2015, Patented.

\* cited by examiner

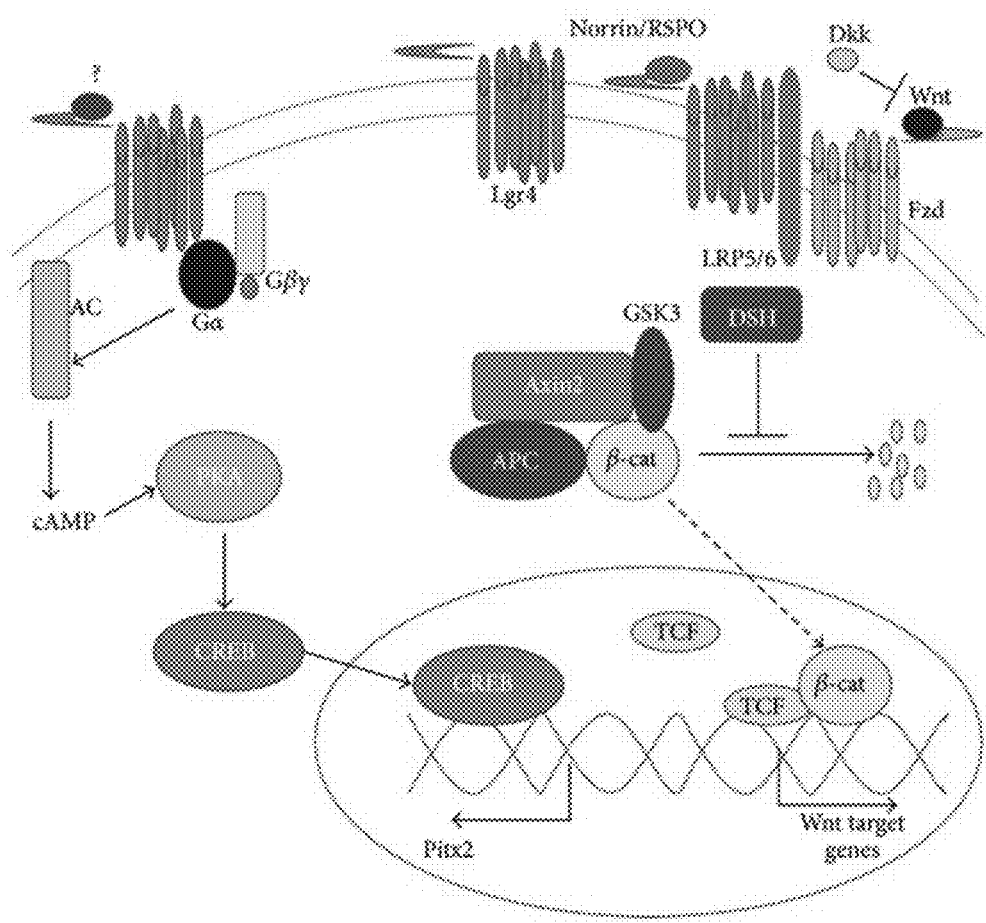
FIG. 5
Right Treated    Left Untreated
P17
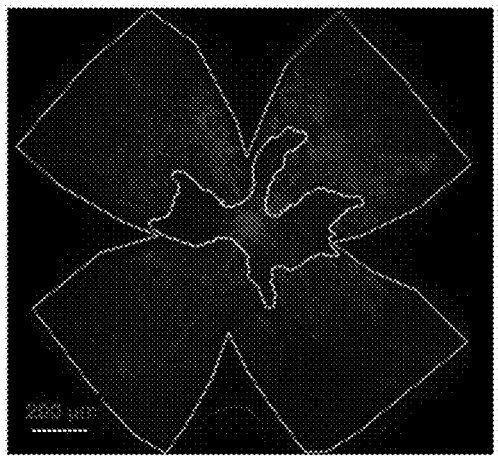    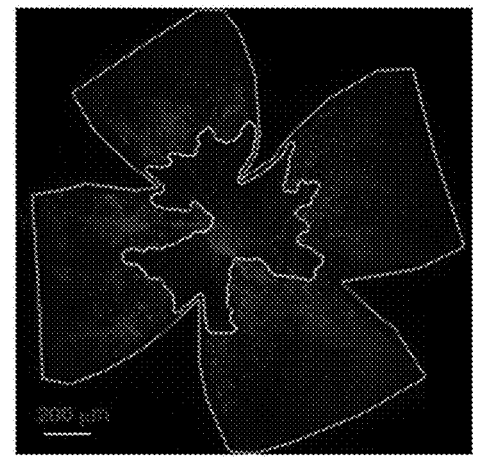
FIG. 6A    FIG. 6B

(12) United States Patent

SYNTHETIC TRUNCATED NORRIN PROTEIN

RELATED APPLICATIONS

This application is a continuation of U.S. application Ser. No. 16/214,225 filed 10 Dec. 2018, which claims priority benefit of U.S. Provisional Application Ser. No. 62/596,349 filed 8 Dec. 2017, and is in turn a continuation-in-part of U.S. application Ser. No. 14/733,876 filed 8 Jun. 2015, now U.S. Pat. No. 10,206,978 B2 issued 19 Feb. 2019; the contents of which are hereby incorporated by reference.

FIELD OF THE INVENTION

The present invention is directed generally to methods of capillary stabilization and vascular regeneration in retinal tissue; and in particular, the use of synthetic norrin to stabilize and produce retinal vasculature.

BACKGROUND OF THE INVENTION

Alterations in norrin function are associated with many pediatric vitreoretinopathies, such as Norrie disease (ND),[1-3] familial exudative vitreoretinopathy (FEVR),[4-5] Coats disease,[6] and retinopathy of prematurity (ROP).[7-9] A unifying characteristic in these diseases is an aberration of retinal vascular development, demonstrating varying degrees of peripheral avascular retina, abnormal vascularization with retinal neovascularization (NV), and subretinal exudation.

At the cellular level, it is widely accepted that disruption of Norrin-Fzd-4 signaling is the key causative factor. Frizzled-4 is one of 11 Frizzled transmembrane receptors known to participate in Wnt signaling. Inside the cell, the Wnt signal can activate three pathways: one canonical (Wnt/β-Catenin) and two noncanonical (Wnt/PCP and Wnt/Ca). There is evidence that norrin may activate all three of these intracellular Wnt pathways.[10-14]

Norrin is a small secreted protein with a cysteine-knot motif.[10,15,16] The cysteine-knot motif is highly conserved in many growth factors including transforming growth factor-β (TGF-β), human chorionic gonadotropin, nerve growth factor, and platelet-derived growth factor. Norrin serves as a ligand for the Frizzled receptor subtype 4 (Fz4). Norrin binds Fz4 with nano molar affinity (Xu, et al., Cell, 2004; 116:883-895; Clevers, Curr Biol, 2004; 14:R436-437; Nichrs, Dev Cell, 2004; 6:453-454). Norrin interaction with Fz4 is dependent on the cell surface receptor LRP5. (Xu, 2004). Frizzled receptors are coupled to the β-catenin canonical signaling pathway. The inactivation of glycogen synthase kinase (GSK) 3β and Axin through frizzled receptor binding stabilizes β-catenin, which subsequently accumulates in the cell nucleus and activates the transduction of target genes that are crucialin the G1-S-phase transition, such as cyclin D1 or c-Myc. (Willert et al., Curr Opin Genet Dev, 1998; 8:95-102). Suppression of norrin activity has been shown to preclude angiogenesis associated with ocular disease (US 2010/0129375).

The structural similarity of norrin to other growth factors suggests that norrin may have a function in addition to traditional Wnt-signaling, despite the fact that norrin is best characterized as a Wnt receptor ligand. This theory is supported by norrin's lack of structural similarity to that of other Wnt proteins.[17] A previous study demonstrated that endogenous expression of norrin inhibits oxygen-induced retinopathy (OIR) in a mouse model.[18] However, the half-life of naturally occurring wild versions of norrin are extremely short and are not effective for use in capillary stabilization and vascular regeneration in retinal tissue Thus, there exists a need for methods of capillary stabilization and vascular regeneration in retinal tissue The present invention is directed to these, as well as other, important needs in the art.

SUMMARY OF THE INVENTION

A method is provided for capillary stabilization and vascular regeneration in retinal tissue that includes exposing the retinal tissue to a norrin and allowing sufficient time for the norrin in the retinal tissue to result in capillary stabilization or vascular regeneration.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

The patent or application file contains at least one drawing executed in color. Copies of this patent or patent application publication with color drawing(s) will be provided by the Office upon request payment of the necessary fee.

These and other aspects of the present invention will be elucidated in the accompanying drawings and following detailed description of the invention.

FIG. 3A illustrates a canonical pathway, FIG. 3B is a non-canonical or planar cell polarity pathway, and FIG. 3C is a Wnt-$Ca^{2+}$ pathway;

FIG. 5 illustrates norrin mediated LGR4 activation on retinal ganglion cells;

FIGS. 6A and 6B show photographs of whole mount of fellow retinas from an OIR mouse at P17, where the right eye) was treated (FIG. 6A) with norrin and the left eye served as the untreated control (FIG. 6B);

DETAILED DESCRIPTION OF THE INVENTION

Figure 1:
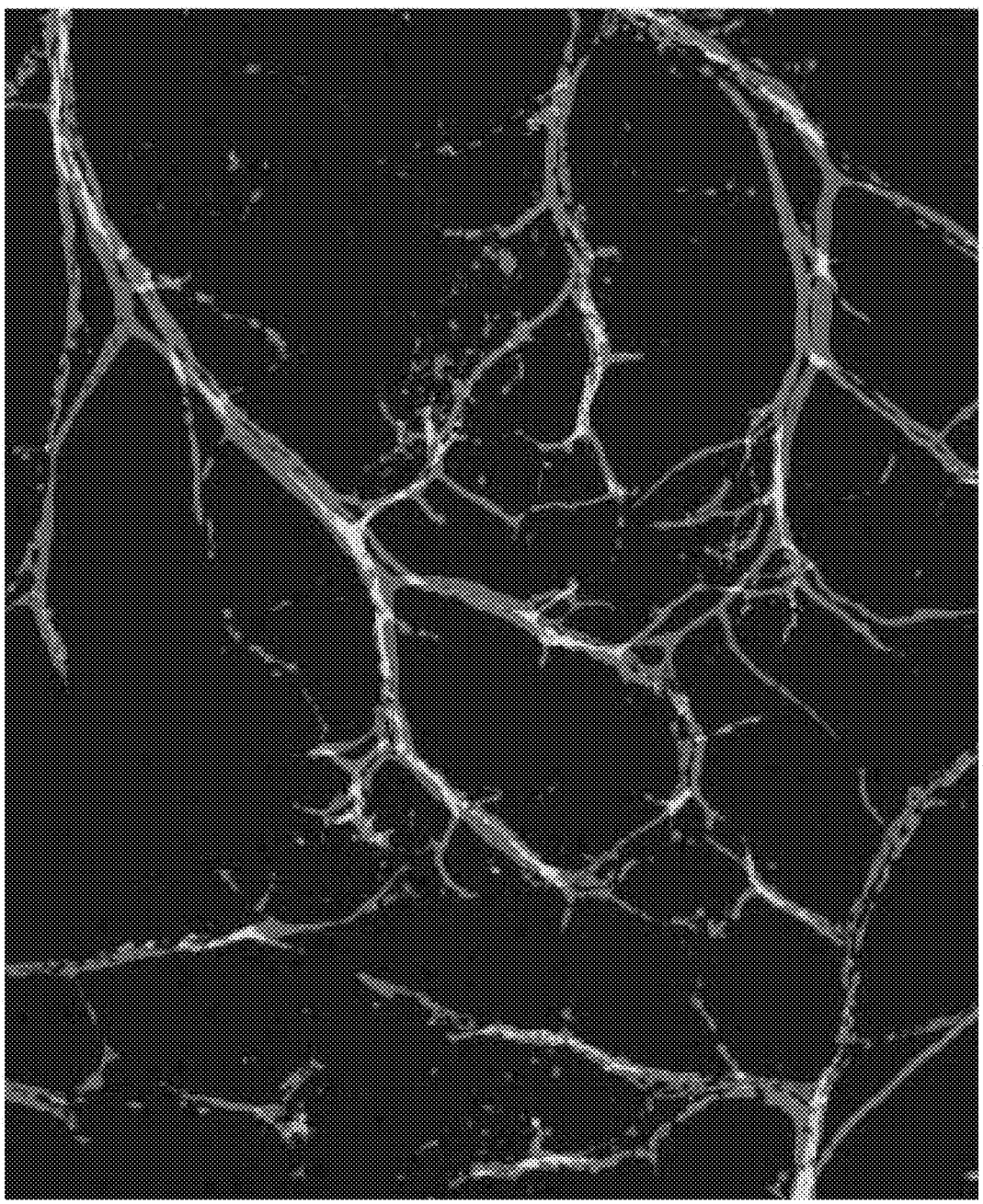
FIG. 1 is a photograph illustrating vascular structure (shown in red) and nerves (shown in green), and are readily seen tracking each other towards their target.
Figure 2A:
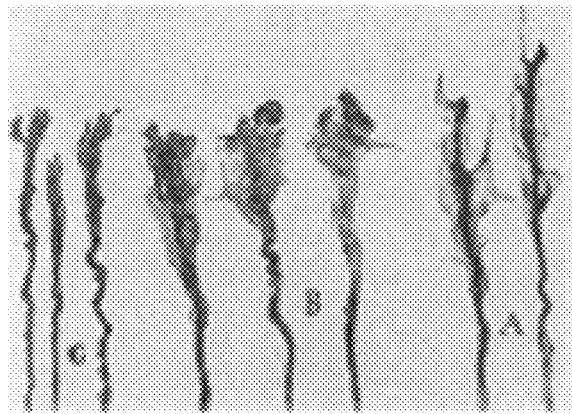
FIGS. 2A-2E illustrate stereotyped axon and vessel navigation where overlapping guidance cues direct growth of both the nerves and blood vessels.
Figure 2B:
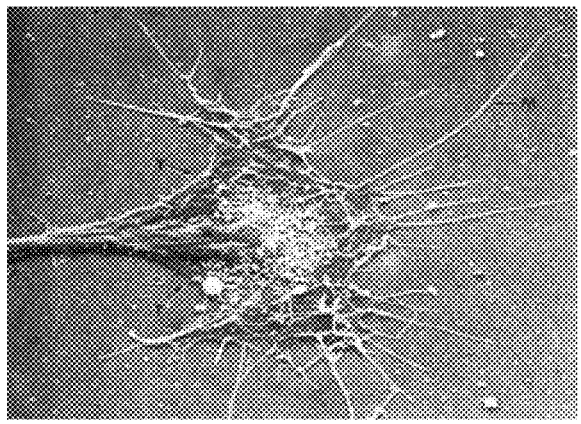
Figure 2C:
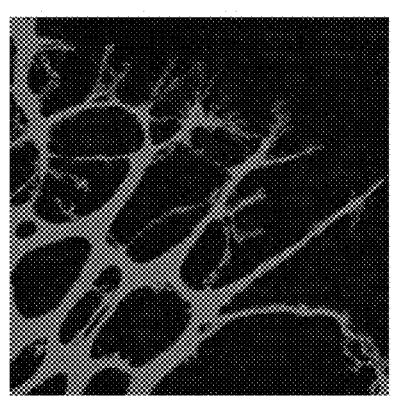
Figure 2D:
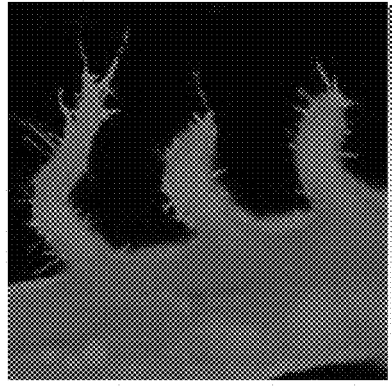
Figure 2E:
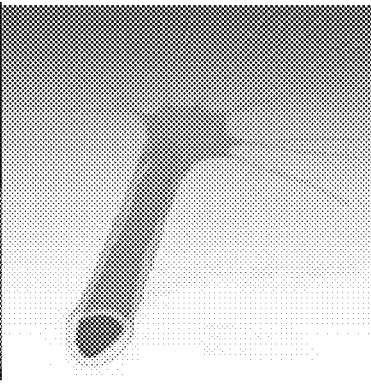

The present invention has utility as a method for capillary stabilization and vascular regeneration in retinal tissue. Inventive embodiments of the disclosed method provide capillary regeneration with a protein that is a truncated norrin protein (synthetic). Embodiments of the truncated norrin protein has a longer half-life in the eye than native wild norrin proteins. A preferred version of the truncated norrin protein lacks a cleavage site that an enzyme in the eye would use to cleave to native norrin proteins and thereby shorten the useful life of the protein.

Embodiments of the inventive method encourage vascular development with an exogenous treatment of truncated norrin that are investigated in oxygen-induced retinopathy (OIR) mice. The therapeutic feasibility of intravitreal injection of the norrin protein and its effect on retinal development by activating Wnt-signaling is also shown.

The following definitions are used herein with respect to the understanding of the present invention.

"Administering" is defined herein as a means of providing norrin protein or a composition containing norrin to a subject retina. Such an administration can be by any route including, without limitation, oral, transdermal (e.g., oral mucosa), by injection (e.g., subcutaneous, intravenous, parenterally, intraperitoneally, intraocular), by inhalation (e.g., oral or nasal), or topical (e.g., eyedrops, cream, etc.). Pharmaceutical preparations are, of course, given by forms suitable for each administration route.

By "alteration" is meant a change (increase or decrease) in the expression levels or activity of a gene or polypeptide as detected by standard art known methods such as those described herein. As used herein, an alteration includes at least a 10% change in expression levels, preferably a 25% change, more preferably a 40% change, and most preferably a 50% or greater change in expression levels.

By "analog" is meant a molecule that is not identical, but has analogous functional or structural features to a norrin protein. For example, a polypeptide analog retains the biological activity of a corresponding naturally-occurring norrin, while having certain biochemical modifications that enhance the analog's function relative to a naturally occurring polypeptide. Such biochemical modifications could increase the analog's protease resistance, solubility, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference status.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means that specifically includes late-phase angiographic posterior and peripheral vascular leakage (LAPPEL). For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of norrin. This portion contains, preferably, at least 40%, 50%, 60%, 70%, 80%, or 90% of the entire length of the 133 amino acid residues of the native human norrin polypeptide. A fragment may contain 40, 50, 60, 70, 80, 90, 100, 110, 120, 130 or even the complete 133 amino acids.

By "truncate" is meant to include a fragment of norrin that has a polypeptide terminus cleavage of the norrin protein of up 40 amino acid residues.

By an "isolated polypeptide" is meant a polypeptide analog of norrin that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

Norrin is meant to define a polypeptide or fragment thereof having at least about 85% amino acid identity to NCBI Accession No. NP_000257.1, as shown below, and having the ability to bind the frizzled-4 receptor of retinal epithelial cells.

gi145577891refINP_000257.11 norrin precursor [*Homo sapiens*] MRKHVLAASFSMLSLLVIMGDTDSKTDSS-FIMDSDPRRCMRHHYVDSISHPLYKCSSKM VLLAR-CEGHCSQASRSEPLVSFSTVLKQPFRSSCHCCRPQT S-KLKALRLRCSGGMRLTAT YRYILSCHCEECNS (SEQ ID NO. 1)

As used herein, "obtaining" as in "obtaining an agent" includes synthesizing, purchasing, or otherwise acquiring the agent.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "treat," "treated," "treating," "treatment," and the like refer to reducing or ameliorating a disorder and/or symptoms associated therewith BRB compromise.

Typically, a therapeutically effective dosage should produce a serum concentration of compound of from about 0.1 ng/ml to about 50-100 μg/ml.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Norrin is a 133 amino acid long protein that is secreted into the extracellular space. Two primary domains define the general norrin protein structure: a signal peptide directs localization of the molecule; and a cysteine-knot motif provides the tertiary confirmation required for frizzled-4 receptor binding. (Meitinger, T, et al, Nat Genet, 1993; 5:376-380; Berger, W, et al, Hum Mol Genet, 1996; 5:51-59). Truncates and fragments of norrin that retain the ability to bind frizzled-4 receptor are operative herein. In some inventive embodiments a truncate or fragment of norrin retains the cysteine-knot motif.

The importance of the cysteine knot-motif is highlighted by computer modeling that demonstrates the requirement of disulfide bonds between the cysteine residues in forming the structural confirmation of norrin. However, mutations in regions other than the cysteine knot-motif produce incomplete protein folding and result in familial exudative vitreoretinopathy (FEVR) and related vitreoretinopathies.

In certain inventive embodiments a −24 residue N-terminus truncate of norrin, with the following amino acid sequence:

KTDSSFIMDSDPRRCMRHHYVDSISHPLYKCSSKMVLLARCEGHCSQASRS EPLVSFSTVLKQPFRSSCHCCRPQTSKLKALRLRCSGGMRLTATYRYILSCHCEECNS (SEQ ID NO: 2) (Accession #Q00604)

It has been found that some fragments and truncations such as SEQ ID NO: 2 have improved solubility compared to norrin.

The invention further embraces variants and equivalents which are substantially homologous to norrin and still retain the ability to selectively bind the frizzled-4 receptor. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid.

The norrin of the present invention is a synthetic norrin retaining frizzled-4 binding properties. It will be recognized in the art that some amino acid sequences of the invention can be varied without significant effect of the structure or function of the protein. Thus, the invention further includes variations of the norrin which show substantial activity; such mutants include deletions, insertions, inversions, repeats, and type substitutions. Norrin mutants operable herein illustratively include amino acid substitutions relative to SEQ ID NO: 1 of R64E. Optionally the biologically active peptide is a multiple mutant relative to SEQ ID NO: 1: R64E: MRKHVLAASFSMLSLLVIMGDTDSKTDSSFIMDSDPRRCMRHHYVDSISHPLYKCSSKM VLLAECEGHCSQASRSEPLVSFSTVLKQPFRSSCHCCRPQTSKLKALRLRCSGGMRLTAT YRYILSCHCEECNS (SEQ ID NO. 3). Optionally the biologically active peptide is a multiple mutant relative to SEQ ID NO: 1: T26A: MRKHVLAASFSMLSLLVIMGDTDSKADSSFIMDSDPRR CMR HHYVDSISHPLYKCSSKM VLLARCEGHCSQASRSEPLVSFSTVLKQPFRSSCHCCRPQTSKLKALRLRCSGGMRLTAT YRYILSCHCEECNS (SEQ ID NO. 4), S28A: MRKHVLAASFSMLSLLVIMGDTDSKTDASFIMDSDPRRCMRHHYVDSISHPLYKCSSK MVLLARCEGHCSQASRSEPLVSFSTVLKQPFRSSCHCCRPQTSKLKALRLRCSGGMRLT ATYRYILSCHCEECNS (SEQ ID NO. 5), S29A: MRKHVLAASFSMLSLLVIMGDTDSKTDSAFIMDSDPRRCMRHHYVDSISHPLYKCSSK MVLLARCEGHCSQASRSEPLVSFSTVLKQPFRSSCHCCRPQTSKLKALRLRCSGGMRLT ATYRYILSCHCEECNS (SEQ ID NO. 6); P36A: MRKHVLAASTSMLSLLVIMGDTDSKTDSSFIMDSDARRCMRHHYVDSISHPLYKCSSK MVLLARCEGHCSQASRSEPLVSFSTVLKQPFRSSCHCCRPQTSKLKALRLRCSGGMRLT ATYRYILSCHCEECNS (SEQ ID NO. 7), R37A: MRKHVLAASFSMLSLLVIMGDTDSKTDSSFIMDSDPARCMRHHYVDSISHPLYKCSSKM VLLARCEGHCSQASRSE- PLVSFSTVLKQPFRSSCHCCRPQTSKLKALRLRCS-GGMRLTATYRYILSCHCEECNS (SEQ ID NO. 8), R38A: MRKHVLAASFSMLSLLVIMGDTDSKTDSSFIMDS-DPRACMRHHYVDSISHPLYKLCSSKM VLLARCEGH-CSQASRSEPLVSFSTVLKQPFRSSCHCCRPQTSKLKA-LRLRCSGGMRLTAT YRYILSCHCEECNS (SEQ ID NO. 9); Y120A: MRKHVLAASFSMLSLLVIMGDTDSKT-DSSFIMDSDPRRCMRHHYVDSISHPLYKCSSKM VLL-ARCEGHCSQASRSEPLVSFSTVLKQPFRSSCHCCRP-QTSKLKALRLRCSGGMRLTAT ARYILSCHCEECNS (SEQ ID NO. 10), R121A: MRKHVLAASFSMLSLLVI-MGDTDSKTDSSFIMDSDPRRCMRHHYVDSISHPLY-KCSSKM VLLARCEGHCSQASRSEPLVSFSTVLKQP-FRSSCHCCRPQTSKLKALRLRCSGGMRLTAT YAYIL-SCHCEECNS (SEQ ID NO. 11), Y122A: MRKHV-LAASFSMLSLLVIMGDTDSKTDSSFIMDSDPRRCM-RHHYVDSISHPLYKCSSKM VLLARCEGHCSQASRSE-PLVSFSTVLKQPFRSSCHCCRPQTSKLKALRLRCS-GGMRLTAT YRAILSCHCEECNS (SEQ ID NO. 12); or H127A: MRKHVLAASFSMLSLLVIMGDTDSKTDSS-FIMDSDPRRCMRHHYVDSISHPLYKCSSKM VLLAR-CEGHCSQASRSEPLVSFSTVLKQPFRSSCHCCRPQT-SKLKALRLRCSGGMRLTAT YRYILSCACEECNS (SEQ ID NO. 13), E129A: MRKHVLAASFSMLSLLVIMGDTD-SKTDSSFIMDSDPRRCMRHHYVDSISHPLYKCSSKM VLLARCEGHCSQASRSEPLVSFSTVLKQPFRSSCHC-CRPQTSKLKALRLRCSGGMRLTAT YRYILSCHCA-ECNS (SEQ ID NO. 14), E130A: MRKHVLAAS- FSML-SLLVIMGDTDSKTDSSFIMDSDPRRCMRHHYVDSI-SHPLYKCSSKM VLLARCEGHCSQASRSEPLVSFST-VLKQPFRSSCHCCRPQTSKLKALRLRCSGGMRLTAT YRYILSCHCEACNS (SEQ ID NO. 15); or combinations thereof. Any amino acid mutated in a multiple mutation is operable as a single mutation. Other sequence mutations operative herein are illustrated in FIGS. 5 and 6 of Small-wood, P M, et al., J Biol Chem, 2007: 282:4057-4068 or Ke, J et al. Genes& Dev. 2013: 27: 2305-2319. These mutations include K86E: MRKHVLAASFSMLSLLVIMGDTD-SKTDSSFIMDSDPRRCMRHHYVDSISHPLYKCSSKM VLLARCEGHCSQASRSEPLVSFSTVLEQPFRSSCHC-CRPQTSKLKALRLRCSGGMRLTATYRYILSCHCEE-CNS (SEQ ID NO. 16), R90E: MRKHVLAASFSMLSLL-VIMGDTDSKTDSSFIMDSDPRRCMRHHYVDSISH-PLYKCSSKM VLLARCEGHCSQASRSEPLVSFSTVL-KQPFESSCHCCRPQTSKLKALRLRCSGGMRLTAT YRYILSCHCEECNS (SEQ ID NO. 17), R97E: MRKHV-LAASFSMLSLLVIMGDTDSKTDSSFIMDSDPRRC-MRHHYVDSISHPLYKCSSKM VLLARCEGHCSQAS-RSEPLVSFSTVLKQPFRSSCHCCEPQTSKLKALRLRC-SGGMRLTAT YRYILSCHCEECNS (SEQ ID NO. 18), K102E: MRKHVLAASFSMLSLLVIMGDTDSKTDSSFI-MDSDPRRCMRHHYVDSISHPLYKCSSKM VLLAR-CEGHCSQASRSEPLVSFSTVLKQPFRSSCHCCRPQT-SELKALRLRCSGGMRLTAT YRYILSCHCEECNS (SEQ ID NO. 19), K104E: MRKHVLAASFSMLSLLVIMGDTD-SKTDSSFIMDSDPRRCMRHHYVDSISHPLYKCSSKM VLLARCEGHCSQASRSEPLVSFSTVLKQPERSSCHC-CRPQTSKLEALRLRCSGGMRLTAT YRYILSCHCEE-CNS (SEQ ID NO. 20), and R115E: MRKHVLAASFSM-LSLLVIMGDTDSKTDSSFIMDSDPRRCMRHHYVD-SISHPLYKCSSKM VLLARCEGHCSQASRSEPLVSFST-VLKQPFRSSCHCCRPQTSKLKALRLRCSGGMELTAT YRYILSCHCEECNS (SEQ ID NO. 21). It is appreciated that other mutations at different amino acid sites are similarly operable. It is further appreciated that mutation of the conserved amino acid at any particular site is preferably mutated to glycine or alanine. It is further appreciated that mutation to any neutrally charged, charged, hydrophobic, hydrophilic, synthetic, non-natural, non-human, or other amino acid is similarly operable. The norrin of the present invention can be recombinant norrin, natural norrin, or synthetic norrin retaining frizzled-4 binding properties. It will be recognized in the art that some amino acid sequences of the invention can be varied without significant effect of the structure or function of the protein. Thus, the invention further includes variations of the norrin which show substantial activity; such mutants include deletions, insertions, inversions, repeats, and type substitutions. A particularly well suited norrin mutant for the present invention is a truncate (SEQ ID NO. 2) with a mutation in at least one position 81-90 of SEQ ID NO: 1 that interferes with protease cleavage of the resulting protein. One or more mutations at positions 84, 85, 86, 87, and 88 SEQ ID NO: 1 results in a norrin truncate-mutant that has a lower molecular weight than native norrin resulting in more rapid diffusion and a longer biological half-life owing to misfit as a substrate for one or more proteases that routinely degrade norrin in vivo. As a result, the norrin-truncate has a half-life that is more than 30% greater than native norrin, and in some embodiments between 50 and 500% greater than native norrin. Trypsin is known to cleavage deactivate native norrin.

Modifications and changes are optionally made in the structure (primary, secondary, or tertiary) of the Norrin protein which are encompassed within the inventive compound that may or may not result in a molecule having similar characteristics to the exemplary polypeptides disclosed herein. It is appreciated that changes in conserved amino acid bases are most likely to impact the activity of the resultant protein. However, it is further appreciated that changes in amino acids operable for receptor interaction, resistance or promotion of protein degradation, intracellular or extracellular trafficking, secretion, protein-protein interaction, post-translational modification such as glycosylation, phosphorylation, sulfation, and the like, may result in increased or decreased activity of an inventive compound while retaining some ability to alter or maintain a physiological activity. Certain amino acid substitutions for other amino acids in a sequence are known to occur without appreciable loss of activity.

In making such changes, the hydropathic index of amino acids are considered. According to the present invention, certain amino acids can be substituted for other amino acids having a similar hydropathic index and still result in a polypeptide with similar biological activity. Each amino acid is assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Without intending to be limited to a particular theory, it is believed that the relative hydropathic character of the amino acid determines the secondary structure of the resultant polypeptide, which in turn defines the interaction of the polypeptide with other molecules. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu).

The norrin and analog: can be further modified to contain additional chemical moieties not normally part of the protein. Those derivatized moieties can improve the solubility, the biological half-life, absorption of the protein, or binding affinity. The moieties can also reduce or eliminate any desirable side effects of the proteins and the like. An overview for those moieties can be found in Remington's Pharmaceutical Sciences, 20th ed., Mack Publishing Co., Easton, Pa. (2000).

The isolated norrin described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. (Zoeller et al., Proc. Nat'l. Acad. Sci. USA 81:5662-5066 (1984) and U.S. Pat. No. 4,588,585).

Norrin truncate of SEQ ID NO: 2 is observed to be effective in increasing cellular junction levels of claudin-5 and VE-cadherins at concentrations of 10 to 1000 ng/ml.

The present invention is also directed to pharmaceutical compositions comprising an effective amount of norrin alone or in combination with a pharmaceutically acceptable carrier, excipient or additive. Particularly favored derivatives are those that increase the bioavailability of norrin administered to a mammal (e.g., by allowing ocularly of choroidal administered norrin to be more readily absorbed into the blood) or which enhance delivery of the norrin to a biological compartment (e.g., the retina) relative to the native protein.

To prepare the pharmaceutical compositions according to the present invention, a therapeutically effective amount of norrin is preferably intimately admixed with a pharmaceutically acceptable carrier according to conventional pharmaceutical compounding techniques to produce a dose. A carrier may take a wide variety of forms depending on the form of preparation desired for administration, e.g., ocular, oral, topical or parenteral, including gels, creams ointments, lotions and time released implantable preparations, among numerous others.

Solutions or suspensions used for ocular, parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Administration in the form of a liquid oral preparation uses a carrier in a form such as suspensions, elixirs and solutions, suitable carriers and additives including water, glycols, oils, alcohols, flavoring agents, preservatives, coloring agents and the like may be used. For solid oral administration, preparations are provided in a form such as powders, tablets, capsules, and for solid preparations such as suppositories, suitable carriers and additives including starches, sugar carriers, such as dextrose, mannitol, lactose and related carriers, diluents, granulating agents, lubricants, binders, or disintegrating agents. If desired, the tablets or capsules may be enteric-coated or sustained release by standard techniques. Norrin is provided in a solid dose is lyophilized form or in pelletized solution droplets.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, poly anhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Formulations suitable for topical administration to the skin may be presented as ointments, creams, gels and pastes including the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

The parenteral preparation can be enclosed in ampoules, disposable syringes or multiple dose vials made of glass or plastic. If administered intravenously, preferred carriers include for example, physiological saline or phosphate buffered saline (PBS).

For parenteral formulations, the carrier will usually comprise sterile water or aqueous sodium chloride solution, though other ingredients including those which aid dispersion may be included. Of course, where sterile water is to be used and maintained as sterile, the norrin and carriers must also be sterilized. Injectable suspensions may also be prepared, in which case appropriate liquid carriers, suspending agents and the like may be employed.

Formulations suitable for parenteral or ocular administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include topical, ocular, parenteral, intramuscular, intravenous, sub-cutaneous, intrachoroidal or, transdermal (which may include a penetration enhancement agent).

Application of the subject therapeutics may be local, so as to be administered at the site of interest. Various techniques can be used for providing the subject norrin at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject norrin, the subject norrin may be painted onto the organ, or may be applied in any convenient way.

Norrin may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment. More specifically, the norrin is administered through an ocular device suitable for direct implantation into the vitreous of the eye. Such devices of the present invention are surprisingly found to provide sustained controlled release of various norrin to treat the eye without risk of detrimental local and systemic side effects. An object of the present ocular method of delivery is to maximize the amount of drug contained in an intraocular device while minimizing its size in order to prolong the duration of the implant. See, e.g., U.S. Pat. Nos. 5,378,475; 5,773,019; 6,001,386; 6,217,895, 6,375,972, and 6,756,058.

Other methods of delivery of norrin include: an ocular delivery system that could be applied to an intra-ocular lens to prevent inflammation or posterior capsular opacification, an ocular delivery system that could be inserted directly into the vitreous, under the retina, or onto the sclera, and wherein inserting can be achieved by injecting the system or surgically implanting the system, a sustained release drug delivery system, and a method for providing controlled and sustained administration of an agent effective in obtaining a desired local or systemic physiological or pharmacological effect comprising surgically implanting a sustained release drug delivery system at a desired location.

Examples include, but are not limited to the following: a sustained release drug delivery system comprising an inner reservoir containing norrin, an inner tube impermeable to the passage of the agent, the inner tube having first and second ends and covering at least a portion of the inner reservoir, the inner tube sized and formed of a material so that the inner tube is capable of supporting its own weight, an impermeable member positioned at the inner tube first end, the impermeable member preventing passage of the agent out of the reservoir through the inner tube first end, and a permeable member positioned at the inner tube second end, the permeable member allowing diffusion of the agent out of the reservoir through the inner tube second end. A method for administering norrin to a segment of an eye, includes implanting a sustained release device to deliver norrin to the vitreous of the eye or choroid, or an implantable, sustained release device for administering a compound of the invention to a segment of an eye or choroid; a sustained release drug delivery device includes a) a drug core containing norrin; b) at least one unitary cup essentially impermeable to the passage of the agent that surrounds and defines an internal compartment to accept the drug core, the unitary cup including an open top end with at least one recessed groove around at least some portion of the open top end of the unitary cup; c) a permeable plug which is permeable to the passage of norrin, the permeable plug is positioned at the open top end of the unitary cup wherein the groove interacts with the permeable plug holding it in position and closing the open top end, the permeable plug allowing passage of the agent out of the drug core, through the permeable plug, and out the open top end of the unitary cup. A sustained release norrin delivery device includes an inner core norrin having a desired solubility and a polymer coating layer, the polymer layer being permeable to norrin, wherein the polymer coating layer completely covers the inner core.

Norrin may be administered as microspheres. For example, norrin may be purchased from R&D Systems, Minneapolis, Minn., or cloned, expressed and purified is loaded into biodegradable microspheres substantially as described by Jiang, C, et al., Mol. Vis., 2007; 13:1783-92 using the spontaneous emulsification technique of Fu, K, et al., J. Pharm. Sci., 2003; 92:1582-91. Microspheres are synthesized and loaded by dissolving 200 mg of 50:50 poly(lactide-co-glycolic acid) (PLGA) in 5 ml of 4:1 volume ratio trifluroethanol:dichloromethane supplemented with 8 mg magnesium hydroxide to minimize protein aggregation during encapsulation. 10 μg norrin may be reconstituted in 300 μl 7 mg bovine serum albumin (BSA) and 100 mg docusate sodium (Sigma-Aldrich, St. Louis, Mo.) dissolved in 3 ml PBS. The solution may be vortexed and poured into 200 ml of 1% (w/v) polyvinyl alcohol (PVA, 88% hydrolyzed) with gentle stirring. Microspheres may be hardened by stirring for three hours, collected by centrifugation, and washed three times to remove residual PVA. If the microspheres are not to be immediately injected they are rapidly frozen in liquid nitrogen, lyophilized for 72 h, and stored in a dessicator at −20° C. Norrin containing microspheres exhibit average diameters of 8 μη as determined by a particle size. Norrin may also be administered by intravitreal injection. For example, norrin in solution, may be packaged into microspheres as described above, or expressed in cells, or in purified form in solution may be exposed to the retina by intravitreal injection substantially as described by Jiang, 2007. Intravitreal injection may be performed under general anesthesia using an ophthalmic operating microscope (Moller-Wedel GmbH, Wedel, Germany) using beveled glass micro-needles with an outer diameter of approximately 100 μm. Microsphere suspensions are prepared in PBS at 2 and 10% (w/v) and briefly vortexed immediately before injection to ensure a uniform dispersion. A 30-gauge hypodermic needle may be used to perforate the sclera 1.5 mm behind the limbus. Five microliters of test sample is optionally injected by way of this passage into the vitreous using a 50 μl Hamilton Syringe (Hamilton Co, Reno, Nev.). To ensure adequate delivery and prevent shock the needle is held in place for one min after the injection is completed and subsequently withdrawn slowly. In addition, paracentesis may be simultaneously performed to relieve pressure and thereby prevent reflux.

Norrin may also be administered by delivery to the retina by a controlled release delivery system. An implantable controlled release delivery system is described in U.S. Patent Application Publication 2005/0281861 and is packaged into such as system at 100 μg per final formulated capsule. For example, a norrin containing drug delivery systems may be placed in the eye using forceps or a trocar after making a 2-3 mm incision in the sclera. Alternatively, no incision may be made and the system placed in an eye by inserting a trocar or other delivery device directly through the eye. The removal of the device after the placement of the system in the eye can result in a self-sealing opening. One example of a device that is used to insert the implants into an eye is disclosed in U.S. Patent Application Publication No. 2004/0054374 which is incorporated herein by reference. The location of the system may influence the concentration gradients of therapeutic component or drug surrounding the element, and thus influence the release rates (e.g., an element placed closer to the edge of the vitreous may result in a slower release rate). Thus, it is preferred if the system is placed near the retinal surface or in the posterior portion of the vitreous.

Preferred unit dosage formulations are those containing a daily dose or unit, daily sub-dose, as hereinabove recited, or an appropriate fraction thereof, of the administered ingredient.

The dosage regimen for norrin invention is based on a variety of factors, including the degree of BRB leakage, the route of administration, ocular volume, macular separation volume, and the particular norrin employed. Thus, the dosage regimen may vary widely, but can be determined routinely using standard methods.

In certain embodiments, norrin is administered once daily; in other embodiments, norrin is administered twice daily; in yet other embodiments, norrin is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

Pharmaceutically acceptable carriers, excipients, or diluents illustratively include saline, buffered saline, dextrose, water, glycerol, ethanol, sterile isotonic aqueous buffer, and combinations thereof.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as PLGA, polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

Examples of preservatives include, but are not limited to, parabens, such as methyl or propyl p-hydroxybenzoate and benzalkonium chloride.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Any of the above-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

When norrin is administered as a pharmaceutical to humans or animals, norrin can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient.

Exemplary ocular dose ranges include 0.00001 mg to 250 mg per day, 0.0001 mg to 100 mg per day, 1 mg to 100 mg per day, 10 mg to 100 mg per day, 1 mg to 10 mg per day, and 0.01 mg to 10 mg per day. A preferred dose of an agent is the maximum that a patient can tolerate and not develop serious or unacceptable side effects. In certain inventive embodiments, the therapeutically effective dosage produces an ocular concentration of norrin of from about 0.1 ng/ml to about 50-100 μg/ml. In certain inventive embodiments, 50 nM to 1 μM of an agent is administered to a subject eye. In related embodiments, about 50-100 nM, 50-250 nM, 100-500 nM, 250-500 nM, 250-750 nM, 500-750 nM, 500 nM to 1 μM, or 750 nM to 1 μM of an norrin is administered to a subject eye.

Determination of an effective amount is well within the capability of those skilled in the art, especially in light of the detailed disclosure provided herein. Generally, an efficacious or effective amount of a norrin is determined by first administering a low dose of the agent(s) and then incrementally increasing the administered dose or dosages until a desired effect (e.g., capillary stabilization and vascular regeneration in retinal tissue) is observed in the treated subject, with minimal or acceptable toxic side effects. Applicable methods for determining an appropriate dose and dosing schedule for administration of a pharmaceutical composition of the present invention are described, for example, in Goodman and Oilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences Philadelphia, Eds., Lippencott Williams & Wilkins (2003 and 2005), each of which is hereby incorporated by reference.

Referring now to the figures, FIG. 1 illustrates how angiogenesis and neurogenesis occur simultaneously, where one process promotes the other. In FIG. 1 vascular structure is shown in red and nerves are in green, and are readily seen tracking each other towards their target. FIGS. 2A-2E illustrate stereotyped axon and vessel navigation where overlapping guidance cues direct growth of both the nerves and blood vessels.

Figures 3A, 3B, 3C:
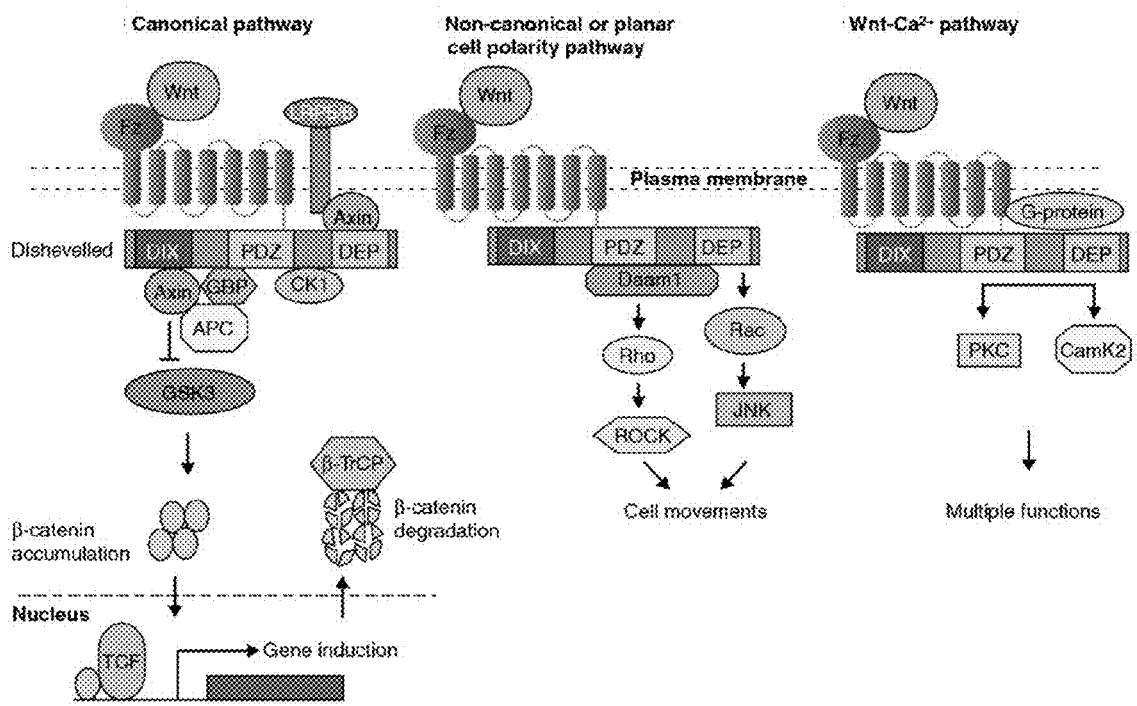
FIGS. 3A-3C illustrate the process of norrin angiogenesis through the Fzd4 receptor on endothelial cells, where
Figure 4:
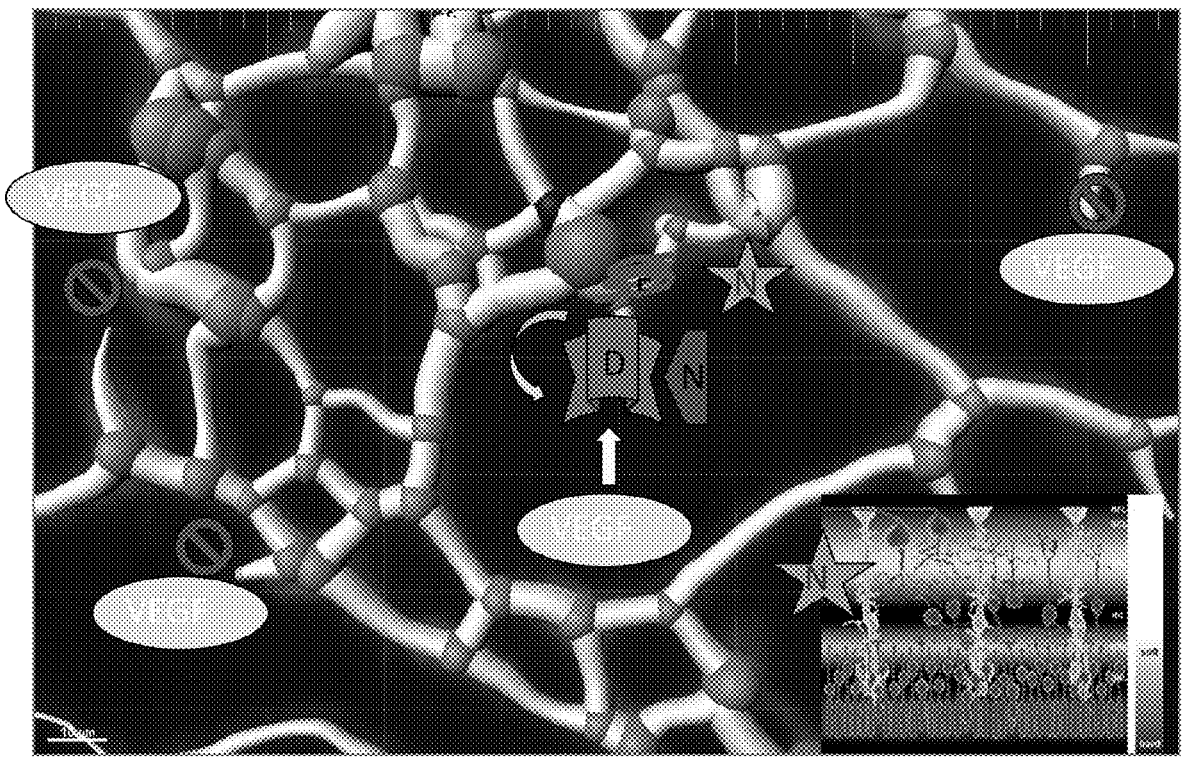
FIG. 4 illustrates norrin-mediated growth of endothelial buds.

As previously described, norrin (Pro-micronorrin) activates Wnt pathways, where with respect to blood vessels the norrin binds the Fzd4 receptor on the retinal endothelial cells, and in neurons the norrin binds the LGR4 receptor on retinal ganglion cells. FIGS. 3A-3C illustrate the process of norrin angiogenesis through the Fzd4 receptor on endothelial cells, where FIG. 3A illustrates a canonical pathway, FIG. 3B is a non-canonical or planar cell polarity pathway, and FIG. 3C is a Wnt-$Ca^{2+}$ pathway. FIG. 4 illustrates norrin-mediated growth of endothelial buds. In modulated angiogenesis the following occurs: endothelial buds (Eb) require VEGF to grow, norrin binds Fzd4 receptor on RECs, activates expression of DLL4 receptor on RECs, DLL4 binds Notch1 which sensitizes Eb to VEGF, and simultaneously desensitizes surrounding Ebs to VEGF. Norrin promotes glial cell growth which is needed for angiogenesis and neurogenesis. Glial cells are a shared pathway for both angiogenesis and neurogenesis. FIG. 5 illustrates norrin mediated LGR4 activation on retinal ganglion cells. Norrin stimulates differentiation and survival of resident stem cells, where chx10/Pax6 co-immunostain is specific for retinal progenitor cells. The AA change is Lys86Pro. which eliminates an internal protease cleavage site in the large loop section of norrin.

The following are in vitro & in vivo examples of how norrin can promote capillary stabilization and vascular regeneration in retinal tissue which are for purposes of illustration, and are not intended to limit the scope of the present invention.

In Vitro Assays

Example 1

C57BL/6J mice were evaluated using a model of oxygen-induced retinopathy (OIR). Test animals were divided in three groups and treated at postnatal day (P) 14 with intravitreal injections of Wnt-signaling modulators (respectively, norrin, Dickkopf-related protein 1 [DKK1], and norrin+DKK1) in one eye. A fourth group of animals were treated with injection of PBS in one eye as well and used as a control group. Areas of avascular retina and neovascular tufts in injected (treated) eyes and noninjected fellow eyes were determined in each of the four groups at P17 (3 days after intravitreal injection) and the difference related to these characteristics was obtained among them. To evaluate the effect of norrin on progression of retinopathy, a fifth litter (eight animals) was also treated with norrin and these retinas were evaluated at different time points.

The oxygen-induced retinopathy (OIR) murine model using C57BL/6J mice neonates used in this example, was previously described in 1994 by Smith et al.[19]. The OIR model shares the two characteristic phases of ROP seen in humans: vasoobliteration (VO) followed by neovascularization (NV)[22]. Therefore, OIR in mice represents a reliable animal model for the study of ROP, as well as other retinal vascular diseases. Briefly, at postnatal day (P) 7, mice were exposed to 75% oxygen for 5 consecutive days. At P12, mice were removed from the oxygen chamber and returned to room air. The mice were divided in three groups, and using a 34-gauge beveled needle (NanoFil; World Precision Instruments, Sarasota, Fla.), received an intravitreal injection of 1 µL of norrin (Norrie disease protein [NDP], 200 ng; R&D Systems, Minneapolis, Minn.) (group 1), Dickkopf-related protein 1 (DKK-1, 30 ng; R&D Systems) (group 2), or the combination of both (NDP 200 ng+DKK-1 30 ng) (group 3) in the right eye at P14. Because each litter might have a different level of OIR depending on the weight[20] (despite all animals being euthanized at the same time point), the fellow eye was not injected, being left as an internal control. In a fourth group, mice underwent intravitreal injection of 1 µL of phosphate-buffered saline (PBS) (Sigma, St. Louis, Mo.) in the right eye as well, to determine the effect of the injection alone, and serve as a control for the effect of intravitreal injection. At P17, mice were euthanized and each of the four groups was subdivided into two subgroups according to weight (5.1 g).

In order to determine the effect of norrin on the natural progression and recovery of vessel abnormalities in the OIR model, another group of eight animals were tested. At P14 each animal received an intravitreal injection of norrin (200 ng) in the right eye. The left eye remained as an uninjected control. Two animals were euthanized at P15, P17, P19, and P21.

All eyes of the test mice were enucleated and fixed in 4% paraformaldehyde (PFA) (Sigma) for 1 hour. Retinas were then isolated, the vasculature was stained with 500 µL lectin solution (10 µg/mL, Isolectin B4-594; Molecular Probes, Eugene, Oreg.) overnight, and whole mounted flat. Images of the whole retinal mounts were taken at ×5 magnification using a fluorescent microscope (Zeiss, Axio Imager; Carl Zeiss Microscopy GmbH, Oberkochen, Germany). The superficial vascular plexus and preretinal neovascular tufts were captured. To evaluate vessel characteristics in higher detail, images were also taken in ×10 and ×20 at the transition of avascular and vascularized areas, as well as the mid periphery. To quantify the avascular areas, an image editor software (CS5; Adobe Photoshop Systems, San Jose, Calif.) was used to merge pictures and calculate the areas based on the total number of pixels.[21] Neovascularization was analyzed using image-processing software (SWIFT_NV; Adobe Photoshop Systems) as previously reported.[22] The avascular area and neovascular tufts were established as a percentage of total retinal area.

At P17, the avascular area in untreated eyes average 23.2% of total retinal area in animals weighing <5.0 g. The animals weighing 5.1 g or more had improved vascularization at the same time point (P17) with an average avascular area of 14.1%, indicating that animals with greater postnatal weight gain have improved vascular recovery. Therefore, the analysis of vascular recovery was segregated into pups weighing <5.0 g) were performed. It is noted that a previous study[20] had indicated that weight may have an influence the severity of vascular abnormalities with various interventions at a single time point (P17). To analyze weight as a factor, a comparison of the level of avascular and neovascular areas of all uninjected fellow eyes to the weight of the respective animal was made. Retinal avascular area and neovascular tufts were compared between fellow eyes of all test groups.

Each animal received injection in one eye (norrin, DKK1, combined, or PBS) and the fellow eye served as the control. The results were analyzed by paired t-test. Although all animals had their retinae evaluated at the same time point (P17), it was observed that their weight had a negative correlation with the severity of avascular area (correlation coecient: −0.48), and a positive correlation with the development of neovascular tufts (correlation coecient: +0.51). This suggested that, for the OIR model, the development and progression of the vessel abnormalities are related not only to the age of the animals, but also to their weight.

Figure 7A:
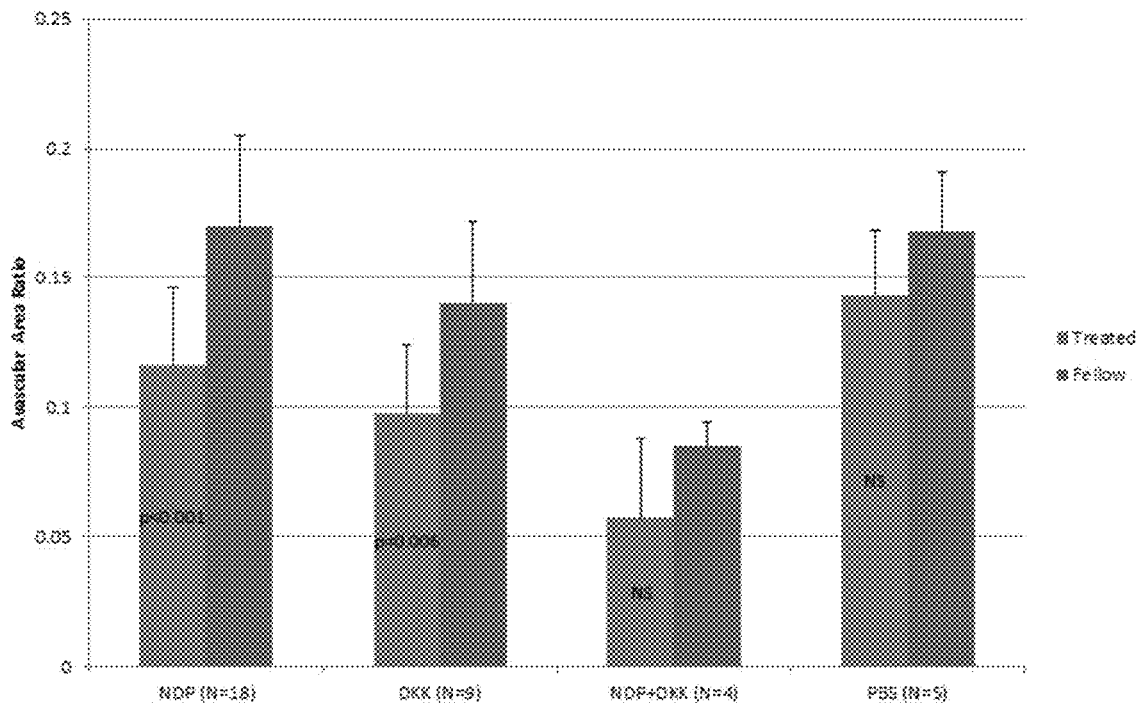
FIGS. 7A and 7B illustrate graph plotting the change in avascular retinas in treated or untreated eyes in mice weighing >5.1 g (FIG. 7A) or <5.0 g (FIG. 7B)
Figure 7B:
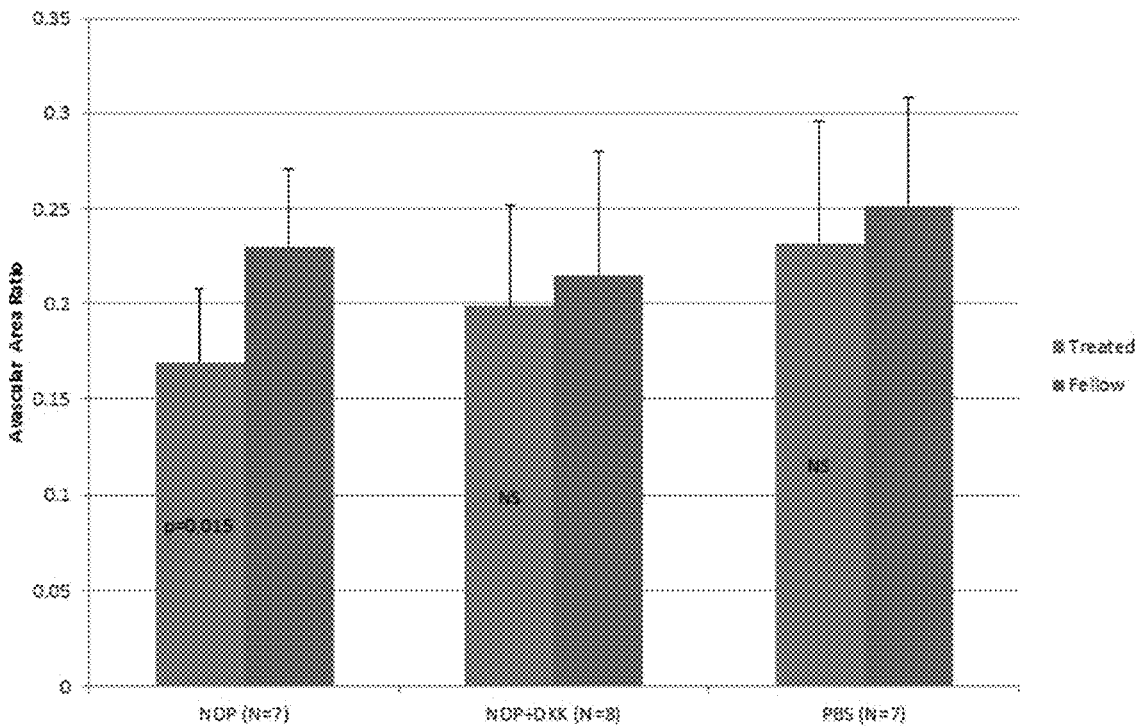

The analysis of retinal whole mounts at P17, in pups treated with intravitreal injection of norrin, show a statistically significant decrease in the avascular area compared to untreated (uninjected) fellow eyes in pups weighing ≥5.1 g ($P<0.001$) and <5.0 g ($P=0.015$), representing a 32% and 27% increase in vascularization, respectively. In contrast, the PBS injection (control group), when compared with the uninjected fellow eye, had minimal impact on vascular growth in both weight groups, demonstrated a 15% (≥5.1 g) and 9.2% (<5.0 g) increase in vascularization, which does not reach statistical significance (FIGS. 6, 7A, 7B).

In order to investigate the role of the Wnt/canonical signaling pathway, canonical signaling was inhibited by intravitreal injection of DKK1, which blocks canonical signal transduction by binding the necessary coreceptor, LRP5. Similar to the norrin-treated eyes, inhibition of the Wnt-canonical signaling by DKK1 shows improved vascular recovery, with an average increase of 28% ($P=0.006$; FIG. 7A). Interestingly, the eyes treated simultaneously with DKK1 and norrin did not result in a statistically significant difference in the avascular area (FIGS. 7A, 7B) compared with uninjected eyes in either weight category. The finding that treatment with norrin alone or DKK1 alone demonstrates a statistically significant reduction in the avascular area of the retina suggests that norrin may act on a nonacnonical pathway to induce retinal vascular recovery.

Figure 8:
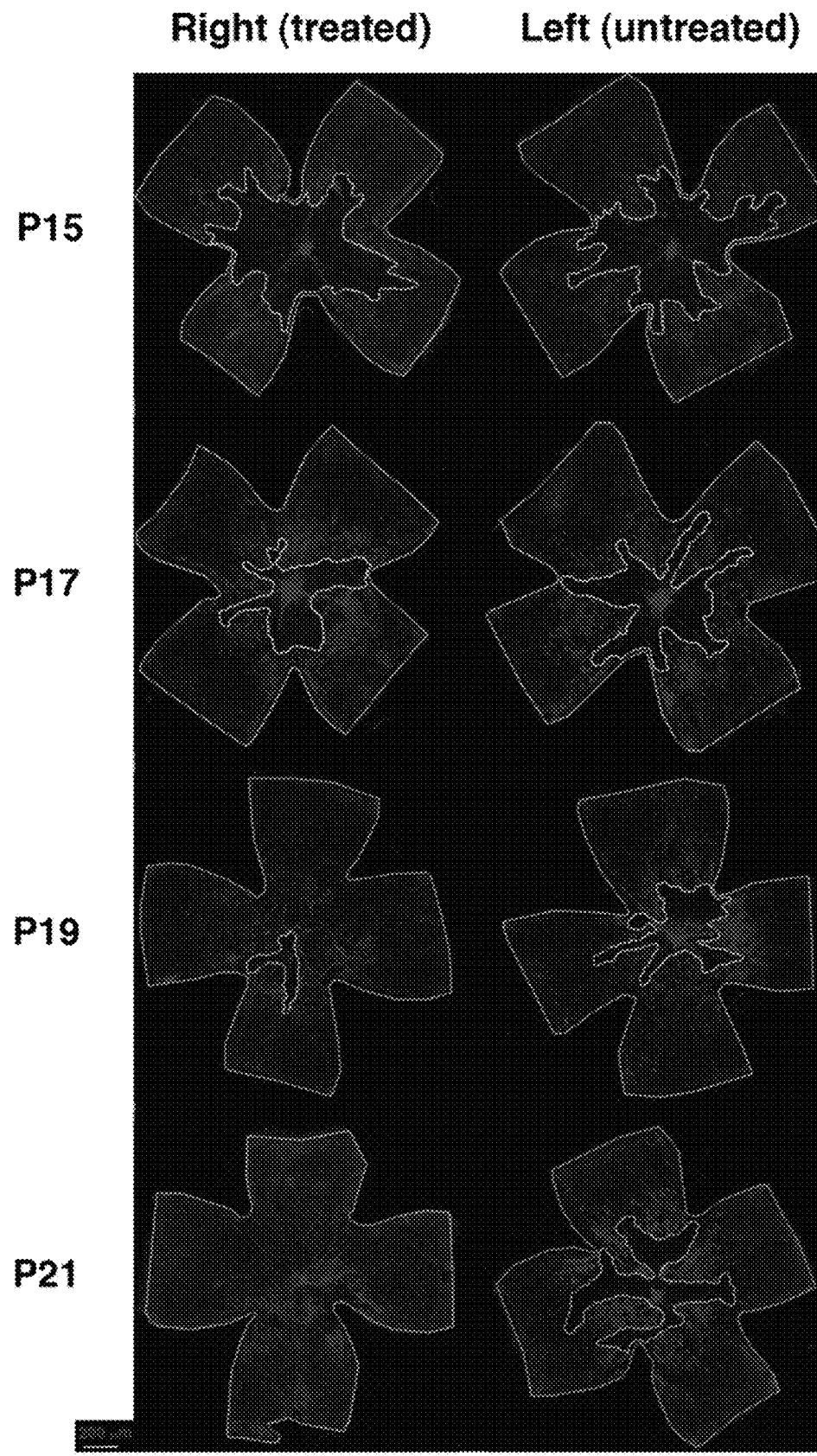
FIG. 8 show photographs of whole mount of fellow retinas from OIR mice at postnatal days 15, 17, 19, and 21, where the right eyes were treated with norrin, and the left eye served as the untreated control.

Animals treated with norrin (200 ng) and euthanized at different time points (P15, P17, P19, P21) show a significant difference in both avascular area and NV between treated and untreated eyes at each time point except P15 (FIG. 8). In addition, the morphology of the neovascular tufts in P17-treated eyes was similar to that of untreated ones at P19, suggesting a faster vascular remodeling with treatment. This trend supports the role of norrin in modulating vascular growth and its positive effect on vascular recovery.

Results of the experiment indicated that modulation of Wnt-signaling consistently showed a statistically significant decrease in the avascular area of the retinas. Treatment with norrin (Wnt-signaling activator) or DKK1 (canonical signaling inhibitor) results in a statistically significant reduction of retinal avascular area compared with control eyes. Neovascular tufts were also reduced in treated eyes, albeit to a lesser extent. Based on the results in may be concluded that modulation of Wnt-signaling improves retinal vascularization and accelerates vascular recovery after induction of retinopathy in the OIR mouse. Activation of Wnt-signaling (norrin) and inhibition of Wnt-canonical signaling (DKK1) result in similar improvement, indicating that norrin promotes improved vascularization, at least in part, by way of noncanonical Wnt-signaling.

Experimental results indicated that norrin is able to rescue mouse retinas from retinopathy by promoting stable vascular growth and decreasing the pathologic secondary changes. Importantly, this effect is possible with norrin given as an intravitreal injection in eyes that have already developed retinopathy. A previous study has shown that endogenous expression of norrin prevents the onset of retinopathy in environments of high oxygen. This same study found that lack of norrin expression may be involved in the development of OIR[18]. The present experiment is the first to demonstrate the ability of exogenous norrin to reverse a vascular disease process and promote normal retinal vasculature.

Both canonical and noncanonical Wnt signal transduction have been implicated in new blood vessel formation, which requires the coordination of endothelial cell division and the morphogenic movement of vessel expansion[23,24]. In an attempt to understand norrin's mechanism of action DKK1 was tested, an inhibitor of the canonical Wnt signaling pathway. It was found that injection of DKK1 at P14 significantly enhanced revascularization of the retina by P17. Since DKK1 inhibits LRP5, a coreceptor needed for canonical Wnt signaling, not to be limited to a particular theory, it is believed that noncanonical Wnt signaling was responsible for the DKK1-induced vascular rescue. Several Wnt ligands that are considered to typically activate canonical signaling have been shown to be upregulated in P17 OIR retinas. Chen et al.[25] have reported an increased expression in Wnt ligands, Wnt 3a, Wnt 7a, and Wnt 10a, in retinas taken from P17 OIR model mice compared with room air controls. Interestingly, they reported no increase in norrin expression in the P17 OIR retinas. The same study also investigated LRP5−/− mice using the OIR and found a decrease in both normal and abnormal vessels at P17. These findings suggest that canonical signal activation plays a role in pathologic angiogenesis.

The improved rescue effect seen with injection of DKK1 supports the belief that the enhanced vascular recovery seen with injection of norrin alone was also due to inducement of one or both of the noncanonical Wnt pathways. Therefore, it was expected to find improved vascular recovery with the coinjection of DKK1 and norrin. Surprisingly, this was not the case. Coinjection of DKK1 and norrin counteracted the angiogenic effect seen when either agent was injected alone. It is believed that this seemingly contradictory result can be explained by the complexity of Wnt signaling.

Which of the three Wnt intracellular pathways transmits the signal may depend on cellular context. The presence of various receptor complex components may determine which pathway is activated. For example, LRP5 is a requirement for canonical signaling in general and TSPAN12 enhances canonical activation by norrin[14]. It appears that norrin has a greater affinity for the Fzd4 receptor alone, and the effective removal of LRP5 by DKK1 increases norrin's binding to the canonical receptor complex. In the combined (norrin+ DKK1) injection, it may be envisioned that norrin binds to a receptor complex that cannot be activated, given that the coreceptor (LRP5) has been bound by DKK1. Therefore, DKK1 binding of LRP5 may result in increased affinity of norrin for the canonical receptor complex, effectively sequestering norrin away from the noncanonical pathways. This would result in decreased noncanonical signaling and defective canonical signaling, essentially canceling any effect of norrin. In this scenario the rescue effect seen with DKK1 alone may be masked by the norrin binding. In other words, the norrin may competitively inhibit binding of the endogenous Wnts to the Fzd4 receptor.

Another complexity that one must consider when evaluating the Wnt intracellular pathways is the regulation of one pathway by others. For instance, it is generally accepted that the noncanonical pathways antagonize the Wnt/β-Catenin pathway and inhibiting canonical signaling can activate Wnt/PCP signaling. For example, Wnt5a activation of the Wnt/JNK (PCP) pathway has been shown to inhibit Wnt/β-Catenin signaling in in vitro reporter assays.

Finally, norrin may also act as a growth factor during retinal development given norrins structural similarity to that of several growth factors. This is supported by the fact that it is an antagonist to TGF-β[28]. Additionally, mutations affecting the receptors for TGF-β (TGFRB1 and TGFRB2) result in a retinal phenotype of FEVR, further supporting the possibility that norrin also functions as a growth factor.

Both norrin and DKK1 reduce the number of neovascular tufts in the OIR model, paralleling the results seen in the promotion of vascular recovery. Again, the combined treatment with norrin and DKK1 resulted in cancellation of any treatment effect. Vascular endothelial growth factor (VEGF) has been shown to be pathologically elevated in infants with ROP[29]. Retinal endothelia cell (REC) culture studies have shown that norrin is able to inhibit the tight junction loosening effect of VEGF on RECs (unpublished data). It is believed that this mode of action is involved in the norrin reduction of NV.

A decrease in neovascular tufts was also seen in the PBS-treated eyes of the larger pups. Indeed, all injected eyes show a trend toward fewer neovascular tufts compared with uninjected eyes. Intravitreal injection per se might have some effect on the vitreous—retina interface, but does not induce significant changes in neovessel formation. In the described experiment, if there was a significant injection effect, this would be noticed in the group that was injected with a combination of norrin and DKK1, which did not occur. For this reason, we believe that the significant result seen in PBS cohort (>5.1 g) was due to the relatively lower number of mice (n=5) rather than to a true protective effect. The low-birth-weight pups also show fewer neovascular tufts in the PBS-treated eyes but it does not reach statistical significance. One reason for the difference between the PBS groups may be the relatively few neovascular tufts developing in the low-birth-weight pups, resulting in a trend toward fewer tufts with injection of any substance, but the low starting number of tufts may prohibit detection of small changes. Historically, evaluation of neovascular tufts results in less consistent data and has value in assessing trends and supporting data but cannot stand alone.

In the OIR murine model used in this study, the maximum severity of the proliferative phase is reached at P17, marked by the greatest extent of pathologic NV and associated plasma leakage from the preretinal neovessels[20]. The data from the present experiment suggest that animal weight plays a role in the severity and timing of onset of OIR as well. Comparing the uninjected fellow eye of all animals with the weight of the corresponding animal, it was observed that mice with lower weight presented fewer neovascular tufts and larger avascular areas at P17, indicating that low weight promotes a delay in both vascular growth and pathologic angiogenesis. Other investigators have also reported that animals with lower weight at birth or slower weight gain velocity, show a delayed onset of OIR and a prolonged course of vascular abnormalities. Stahl et al.[20] showed that mice with body weights between 5 and 7.5 g at P17 displayed the highest amount of NV, whereas mice with either <5 g or >7.5 g body weight at P17 showed significantly lower severity of NV. With these findings, it seems reasonable that mice with lower weight at birth and slower growth behave like normal-weight pups but at an earlier postnatal age, resulting in the postponement of vascular abnormalities involved in OIR, such as neovascular tufts.

Once the vascular differences seen with weights of the mice were identified, an understanding of the natural progression of vascular growth and pathologic changes in the presence and absence of norrin treatment was sought. Therefore, littermates were treated with intravitreal norrin in the right eye at P14 (fellow eye uninjected) and evaluated at sequential time points (P15, P17, P19, P21). Despite the low sample number, interesting findings were obtained: at P15 the avascular area was large and the neovascular tufts were very few, both in treated and untreated eyes, representing vascular obliteration (FIG. 8). By P17 the avascular area was smaller in treated eyes and the neovascular tufts were fewer as compared with the fellow (uninjected) eye. The norrin-treated eye at P19 shows almost full revascularization of the retina. This is in stark contrast to the uninjected fellow eye. The most remarkable difference was observed at P21. In addition to significant vascular recovery in the norrin-treated eyes, compared with uninjected control eyes, the P21 pups had a significant difference in weight gain (6.7 and 4.7 g). The normal-weight mouse (6.7 g) had fewer vascular abnormalities in both eyes (norrin and uninjected), as expected, given the natural vascular recovery in the OIR model at this time point. However, the lower-weight mouse (4.7 g) showed a large difference in vascular recovery between the fellow eyes. The norrintreated eye had nearly complete revascularization, whereas the untreated fellow eye still possessed a very large avascular area and neovascular tufts. These findings again support that poor weight gain postpones the development and natural course of OIR. However, norrin has an even more remarkable effect in these low-weight animals, possibly by promoting and accelerating normal vessel development. This finding has great importance in regard to premature infants at the highest risk for the development of retinopathy of prematurity and reinforces the potential use of norrin in humans.

The highly localized expression of norrin in the retina, cochlea, and central nervous system during development suggests a highly specific role for norrin in the appropriate maturation of these particular tissues. There are other non-specific Wnt ligands that are able to bind both the Fzd4 and LRP5 (receptor and coreceptor for norrin), but these have been shown to be upregulated during pathologic angiogenesis.[29] Clinical studies and animal models clearly show that lack of norrin expression in the eye results in severe abrogation of retinal development, indicating that Wnt pathway activation alone (by other Wnt ligands) is not sufficient for normal retinal development and vasculaturization.[30-33]

Example 2

Bosma et al.[34] have shown that the breakdown of the blood-brain barrier (BBB) or inner blood-retinal barrier (BRB), induced by pathologically elevated levels of vascular endothelial growth factor (VEGF) or other mediators, can lead to vasogenic edema and significant clinical problems such as neuronal morbidity and mortality, or vision loss. Restoration of the barrier function with corticosteroids in the brain, or by blocking VEGF in the eye are currently the predominant treatment options for brain edema and diabetic macular edema, respectively. However, corticosteroids have side effects, and VEGF has important neuroprotective, vascular protective and wound healing functions, implying that long-term anti-VEGF therapy may also induce adverse effects. Bosma et al.[34] show that targeting downstream effector proteins of VEGF and other mediators that are directly involved in the regulation of BBB and BRB integrity provide more attractive and safer treatment options for vasogenic cerebral edema and diabetic macular edema. The endothelial cell-specific protein plasmalemma vesicle-associated protein (PLVAP), a protein associated with trans-endothelial transport, emerges as a candidate for this approach. PLVAP is expressed in a subset of endothelial cells throughout the body where it forms the diaphragms of caveolae, fenestrae and trans-endothelial channels. However, PLVAP expression in brain and eye barrier endothelia only occurs in pathological conditions associated with a compromised barrier function such as cancer, ischemic stroke and diabetic retinopathy.[34]

Experiments were conducted to show the use of norrin for suppression of plasmalemma vesicle-associated protein (PLVAP) expression in human retinal microvascular endothelial cells (HRMEC)

Figure 9:
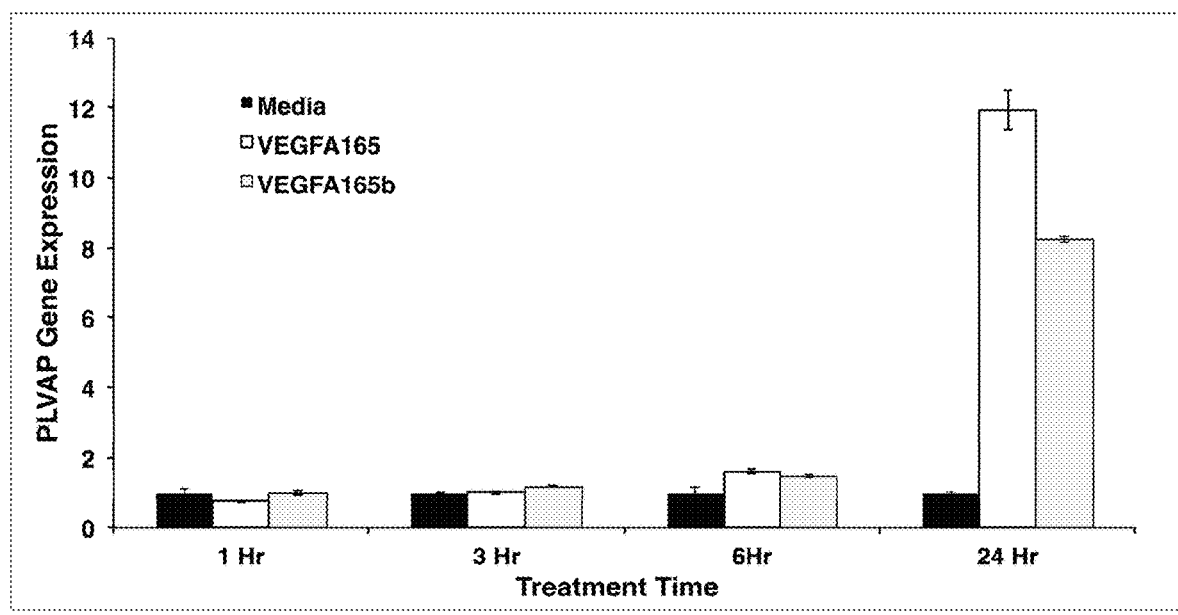
FIG. 9 illustrates a bar graph showing PLVAP was significantly increased by approximately a factor of ten after twenty-four hours of VEGFA (Vascular endothelial growth factor A) treatment.

In a first experiment, HRECS were treated with 100 ng/ml (approximately 5000 pM) of VEGFA (or b-isoform) for twenty four hours where the media is 2.5% FBS (no HC EndoGro). FIG. 9 shows that PLVAP was significantly increased by approximately a factor of 10 after twenty four hours of VEGFA (Vascular endothelial growth factor A) treatment.

Figure 10:
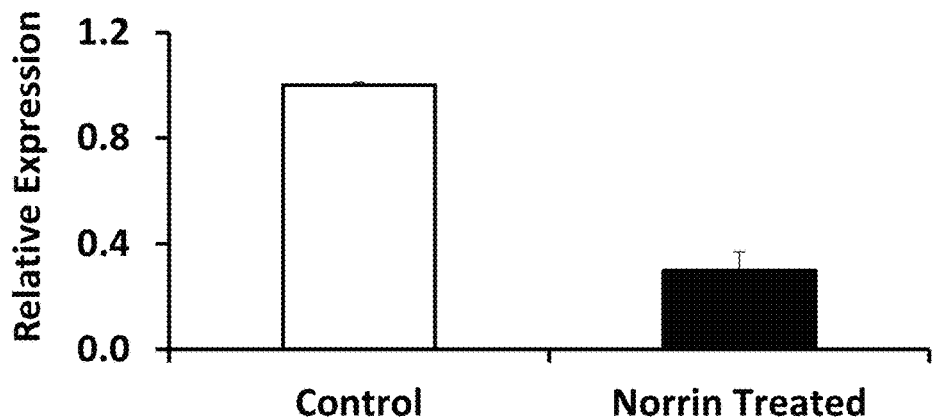
FIG. 10 illustrates a bar graph showing PLVAP gene expression is decreased by approximately three times in response to treatment with norrin.
Figure 11:
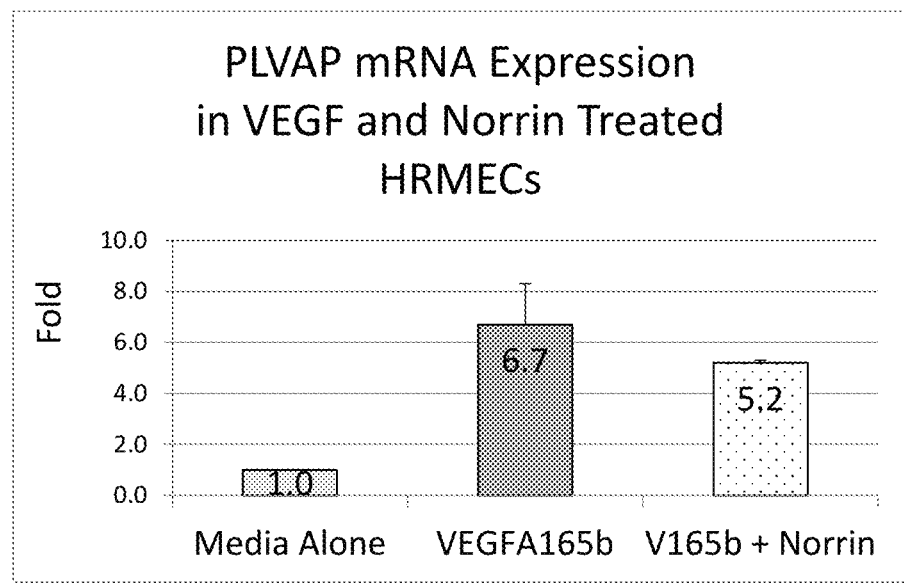
FIG. 11 illustrates a bar graph that shows VEGFA165b significantly increases PLVAP expression as compared to untreated media, while the use of norrin only had a slight effect in decreasing VEGFA165b induced PLVAP expression.

In a second experiment a media composed of 2.5% FBS (no HC EndoGro) is treated for twenty four hours with [VEGFA165b (100 ng/ml)]+/−[RnD norrin (200 ng/ml)]. As shown in FIG. 10, PLVAP gene expression is decreased by approximately three times (i.e., under one third of the PLVAP gene expression in the control) in response to treatment with norrin. FIG. 11 shows VEGFA165b significantly increases PLVAP expression as compared to untreated media, however the use of norrin only had a slight effect in decreasing VEGFA165b induced PLVAP expression.

Figure 12:
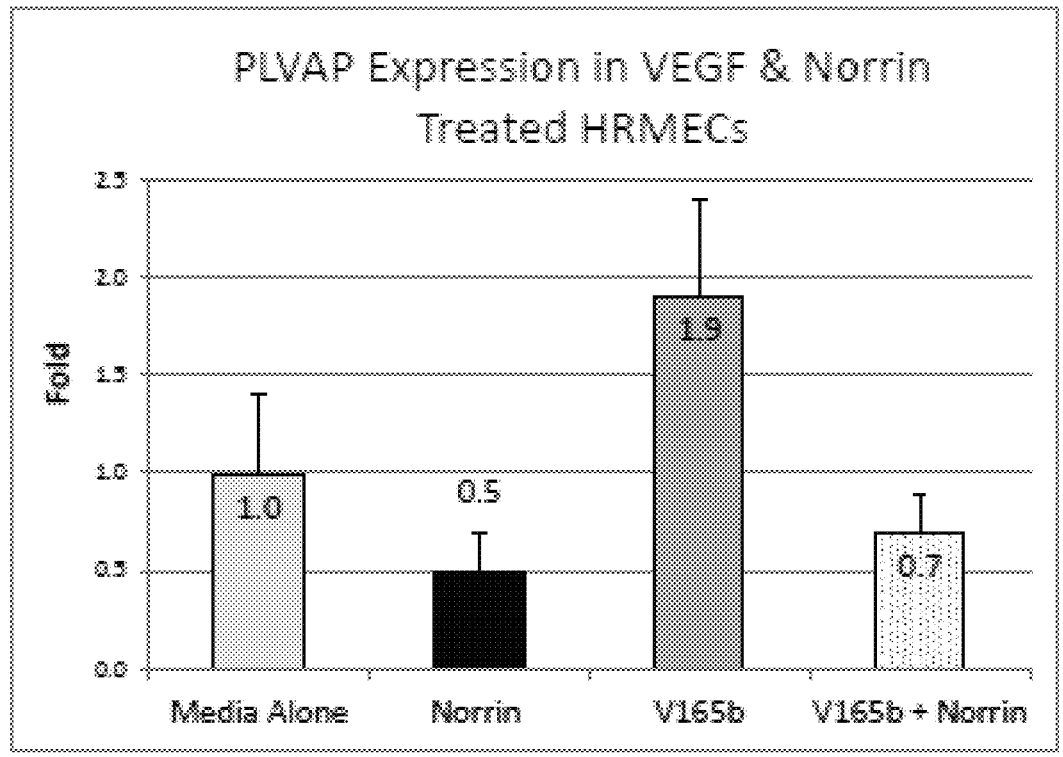
FIG. 12 illustrates a bar graph that shows norrin significantly decreasing PLVAP expression by approximately two times, and while VEGFA165b significantly increases PLVAP expression, the introduction of norrin significantly decreases VEGFA165b induced PLVAP expression (p=0.02)

In a third experiment a media composed of 2.5% FBS (no HC EndoGro) is treated for twenty four hours with [VEGFA165b (25 ng/ml)]+/−[RnD norrin (200 ng/ml)]. FIG. 12 shows that norrin significantly decreases PLVAP expression by approximately two times, and while VEGFA165b significantly increases PLVAP expression, the introduction of norrin significantly decreases VEGFA165b induced PLVAP expression (p=0.02).

Example 3

Figure 13:
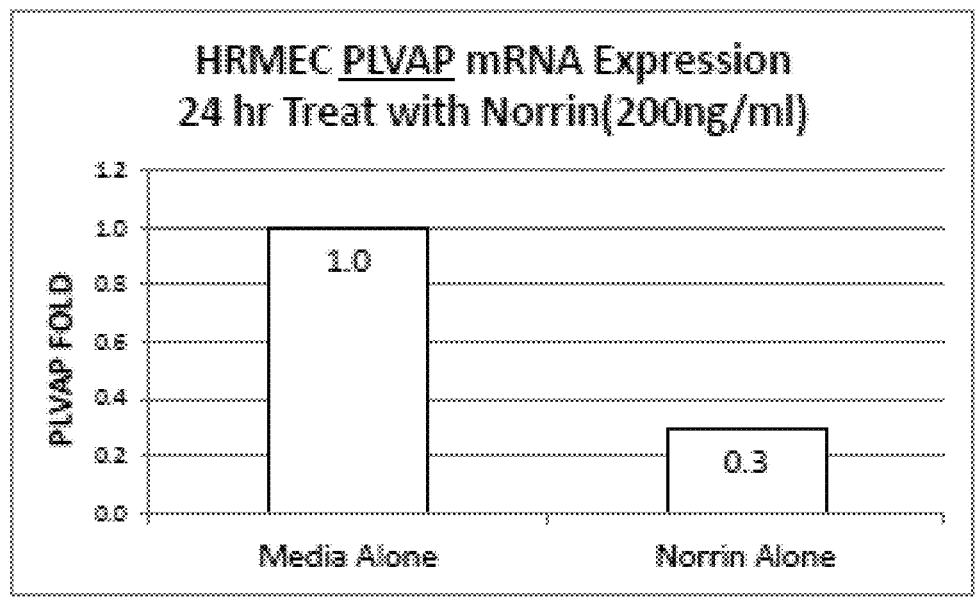
FIGS. 13 and 14 illustrate bar graphs that show the results of PLVAP mRNA expression after treatment for twenty-four hours with norrin, where in FIG. 13 norrin decreases expression of PLVAP, while in FIG. 14 VEGFA165b increases PLVAP expression, while norrin diminishes the increase of PLVAP caused by the VEGFA165b.
Figure 14:
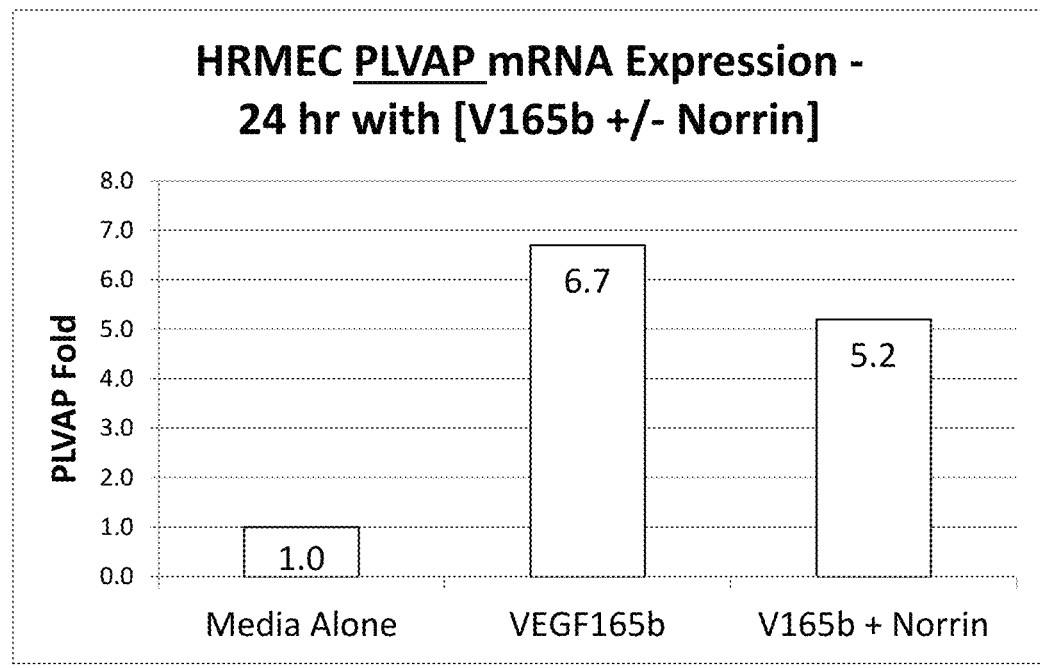

Conducted experiments show that norrin works in non-tight-junction protein pathways as well to reduce macular edema and inflammation. FIGS. 13 and 14 illustrate the results of PLVAP mRNA expression after treatment for twenty four hours with norrin. In FIG. 13 norrin decreases expression of PLVAP. In FIG. 14 VEGFA165b increases PLVAP expression, while norrin diminishes the increase of PLVAP caused by the VEGFA165b.

Based on the experimental findings presented herein, norrin may represent a unique molecule that is able to function as both a Wnt-ligand and a growth factor and regulate angiogenesis in a fashion that mimics that seen in the developing eye. This has significant implication in the treatment of many eye diseases characterized by anomalous vasculature, including avascular retina, vascular permeability, capillary drop-out, and NV. These conditions are seen in the inherited vitreoretinopathies, such as FEVR, Norrie disease, and persistent fetal vasculature, as well as retinopathy of prematurity, diabetic retinopathy, and retinal artery and vein occlusions.

Wide-field fluorescein angiography is noted to be particularly useful in the identification of areas of capillary inflammatory changes and late-phase angiographic posterior and peripheral vascular leakage (LAPPEL). Accordingly, LAPPEL is used in some inventive embodiments as a precursor in pathogenesis of capillary dropout and a marker of endothelial cell inflammation in the retina.[35]

As a person skilled in the art will recognize from the previous detailed description and from the figures and claims, modifications and changes can be made to the preferred embodiments of the invention without departing from the scope of this invention defined in the following claims.

REFERENCES

1. Schuback D E., Chen Z Y., Craig I W., Breakeeld X O., Sims K B.; Mutations in the Norrie disease gene. Hum Mutat. 1995; 5: 285-292.
2. Meindl A., Berger W., Meitinger T.; Norrie disease is caused by mutations in an extracellular protein resembling C-terminal globular domain of mucins. Nat Genet. 1992; 2: 139-143.
3. Berger W., van de Pol D., Warburg M.; Mutations in the candidate gene for Norrie disease. Hum Mol Genet. 1992; 1: 461-465.
4. Shastry B S., Hejtmancik J F., Plager D A., Hartzer M K., Trese M T.; Linkage and candidate gene analysis of X-linked familial exudative vitreoretinopathy. Genomics. 1995; 27: 341-344.
5. Chen Z Y., Battinelli E M., Fielder A.; A mutation in the Norrie disease gene (NDP) associated with X-linked familial exudative vitreoretinopathy. Nat Genet. 1993; 5: 180-183.
6. Black G C., Perveen R., Bonshek R.; Coats' disease of the retina (unilateral retinal telangiectasis) caused by somatic mutation in the NDP gene: a role for norrin in retinal angiogenesis. Hum Mol Genet. 1999; 8: 2031-2035.
7. Talks S J., Ebenezer N., Hykin P.; De novo mutations in the 5' regulatory region of the Norrie disease gene in retinopathy of prematurity. J Med Genet. 2001; 38: E46.
8. Hutcheson K A., Paluru P C., Bernstein S L.; Norrie disease gene sequence variants in an ethnically diverse population with retinopathy of prematurity. Mol Vis. 2005; 11: 501-508.
9. Hiraoka M., Berinstein D M., Trese M T., Shastry B S.; Insertion and deletion mutations in the dinucleotide repeat region of the Norrie disease gene in patients with advanced retinopathy of prematurity. J Hum Genet. 2001; 46: 178-181.
10. Xu Q., Wang Y., Dabdoub A.; Vascular development in the retina and inner ear: control by Norrin and Frizzled-4, a high-anity ligand-receptor pair. Cell. 2004; 116: 883-895.
11. Descamps B., Sewduth R., Ferreira Tojais N.; Frizzled 4 regulates arterial network organization through noncanonical Wnt/planar cell polarity signaling. Circ Res. 2012; 110: 47-58.
12. Yao R., Natsume Y., Noda T.; MAGI-3 is involved in the regulation of the JNK signaling pathway as a scaffold protein for frizzled and Ltap. Oncogene. 2004; 23: 6023-6030.
13. Robitaille J., MacDonald M L., Kaykas A.; Mutant frizzled-4 disrupts retinal angiogenesis in familial exudative vitreoretinopathy. Nat Genet. 2002; 32: 326-330.
14. Junge H., Yang S., Burton J.; TSPAN12 regulates retinal vascular development by promoting norrin, but not Wnt-induced FZD4/β-catenin signaling. Cell. 2009; 139: 299-311.
15. Berger W.; Molecular dissection of Norrie disease. Acta Anat (Basel). 1998; 162: 95-100.

16. Black G., Redmond R M.; The molecular biology of Norrie's disease. Eye. 1994; 8: 491-496.
17. McDonald N Q., Hendrickson W A.; A structural superfamily of growth factors containing a cystine knot motif. Cell. 1993; 73: 421-424.
18. Ohlmann A., Seitz R., Braunger B., Seitz D., Bosl M R., Tamm E R.; Norrin promotes vascular regrowth after oxygeninduced retinal vessel loss and suppresses retinopathy in mice. J Neurosci. 2010; 30: 183-193.
19. Smith L E., Wesolowski E., McLellan A.; Oxygen-induced retinopathy in the mouse. Invest Ophthalmol Vis Sci. 1994; 35: 101-111.
20. Stahl A., Chen J., Sapieha P.; Postnatal weight gain modies severity and functional outcome of oxygeninduced proliferative retinopathy. Am J Pathol. 2010; 177: 2715-2723.
21. Connor K M., Krah N M., Dennison R J.; Quantication of oxygen-induced retinopathy in the mouse: a model of vessel loss, vessel regrowth and pathological angiogenesis. Nat Protoc. 2009; 4: 1565-1573.
22. Stahl A., Connor K M.; Sapieha P Computer-aided quantication of retinal neovascularization. Angiogenesis. 2009; 12: 297-301.
23. Zeng G.; Orientation of endothelial cell division is regulated by VEGF signaling during blood vessel formation. Blood. 2007; 109: 1345-1352.
24. Dejana E.; The role of Wnt signaling in physiological and pathological angiogenesis. Circ Res. 2010; 107: 943-952.
25. Chen J., Stahl A., Krah N M.; Wnt signaling mediates pathological vascular growth in proliferative retinopathy. Circulation. 2011; 124: 1871-1881.
26. Rao T P., Kuvhl M.; An updated overview on Wnt signaling pathways. A prelude for more. Circ Res. 2010; 106: 1798-1806.
27. Mikels A., Nusse R.; Puried Wnt5a protein activates or inhibits β-Catenin-TCF signaling depending on receptor context. PLoS Biol. 2006; 4: 570-582.
28. Tamm E., Ohlmann A.; Norrin in the treatment of diseases associated with an increased TGF-beta activity. European patent application EP20090798920. Sep. 28, 2011.
29. Sonmez K., Drenser K., Capone A., Trese M T; Vitreous levels of stromal cell-derived factor 1 and vascular endothelial growth factor in patients with retinopathy of prematurity. Ophthalmology. 2008; 115: 1065-1070. [CrossRef] [PubMed]
30. Robitaille J., Zheng B., Wallace K.; The role of Frizzled-4 mutations in familial exudative vitreoretinopathy and Coats disease. Br J Ophthalmol. 2011; 95: 574-579.
31. Chen Y., Hu Y., Zhou T.; Activation of the Wnt pathway plays a pathogenic role in diabetic retinopathy in humans and animal models. Am J Pathol. 2009; 175: 2676-2685.
32. Wu W C., Drenser K., Trese M T, Capone A., Jr Dailey W.; Retinal phenotype-genotype correlation of pediatric patients expressing mutations in the Norrie disease gene. Arch Ophthalmol. 2007; 125: 225-230.
33. Chen J., Stahl A., Krah N M; Retinal expression of Wnt-pathway mediated genes in low-density lipoprotein receptor-related protein 5 (Lrp5) knockout mice. PLoS One. 2012; 7: e0030203.
34. Esmeralda K. Bosma1, Cornelis J. F. van Noorden, Reinier O. Schlingemann, and Ingeborg Klaassen; The role of plasmalemma vesicle-associated protein in pathological breakdown of blood-brain and blood-retinal barriers: potential novel therapeutic target for cerebral edema and diabetic macular edema. Fluids and Barriers of the CNS. 2018; 15:24 https://doi.org/10.1186/s12987-018-0109-2.
35. Thanos A., Todorich B., and Trese M T; A Novel Approach to Understanding Pathogenesis and Treatment of Capillary Dropout in Retinal Vascular Diseases. Ophthalmic Surgery, Lasers and Imaging Retina. 2016; 47 (3): 288-292

The invention claimed is:

1. A synthetic truncated norrin protein comprising:
a norrin truncate protein having at least 85% identity to SEQ ID. NO. 1 with 24 residues deleted from the N-terminus relative to SEQ ID. NO. 1 that retains a cysteine-knot motif and frizzled-4 binding properties with a mutation in the cysteine-knot motif in at least one position of amino acids 81-90 of SEQ ID. NO. 1 that interferes with protease cleavage of the resulting protein.

2. The norrin truncate of claim 1 further comprising one or more mutations at positions 84, 85, 86, 87, and 88 of SEQ ID. NO. 1.

3. The norrin truncate of claim 1 wherein the mutation in the cysteine-knot motif in at least one position 81-90 of SEQ ID. NO. 1 lowers the molecular weight of the resulting protein relative to native norrin, thereby increasing the solubility and the rate of diffusion of the resulting protein relative to native norrin.

4. The norrin truncate of claim 1 wherein the biological half-life is more than 30% greater than a biological half-life of native norrin.

5. The norrin truncate of claim 1 wherein the biological half-life is between 50% and 500% greater than a biological half-life of native norrin.

6. The norrin truncate of claim 1 further comprising at least one amino acid substitution wherein the substituting amino acid has a hydropathic index within ±2 of the hydropathic index of the substituted amino acid.

7. The norrin truncate of claim 6 wherein the substituting amino acid has a hydropathic index within ±1 of the hydropathic index of the substituted amino acid.

8. The norrin truncate of claim 6 wherein the substituting amino acid has a hydropathic index within ±0.5 of the hydropathic index of the substituted amino acid.

9. The norrin truncate of claim 8 wherein the at least one amino acid substitution is one of (original residue: substitution): (Ala: Gly or Ser), (Arg: Lys), (Asn: Gln or His), (Asp: Glu or Cys or Ser), (Gln: Asn), (Glu: Asp), (Gly: Ala), (His: Asn or Gln), (Ile: Leu or Val), (Leu: Ile or Val), (Lys: Arg), (Met: Leu or Tyr), (Ser: Thr), (Thr: Ser), (Trp: Tyr), (Tyr: Trp or Phe), or (Val: Ile or Leu).

10. The norrin truncate of claim 1 further comprising at least one additional chemical moiety not naturally part of the resulting protein.

* * * * *

SEQUENCE LISTING

<160> NUMBER OF SEQ ID NOS: 21

<210> SEQ ID NO 1
<211> LENGTH: 133
<212> TYPE: PRT
<213> ORGANISM: Homo sapiens

<400> SEQUENCE: 1

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110
```

```
Gly Met Arg Leu Thr Ala Thr Tyr Arg Tyr Ile Leu Ser Cys His Cys
        115                 120                 125

Glu Glu Cys Asn Ser
        130

<210> SEQ ID NO 2
<211> LENGTH: 109
<212> TYPE: PRT
<213> ORGANISM: Artificial sequence
<220> FEATURE:
<223> OTHER INFORMATION: Synthetic

<400> SEQUENCE: 2

Lys Thr Asp Ser Ser Phe Ile Met Asp Ser Asp Pro Arg Arg Cys Met
1               5                   10                  15

Arg His His Tyr Val Asp Ser Ile Ser His Pro Leu Tyr Lys Cys Ser
            20                  25                  30

Ser Lys Met Val Leu Leu Ala Arg Cys Glu Gly His Cys Ser Gln Ala
        35                  40                  45

Ser Arg Ser Glu Pro Leu Val Ser Phe Ser Thr Val Leu Lys Gln Pro
    50                  55                  60

Phe Arg Ser Ser Cys His Cys Cys Arg Pro Gln Thr Ser Lys Leu Lys
65                  70                  75                  80

Ala Leu Arg Leu Arg Cys Ser Gly Gly Met Arg Leu Thr Ala Thr Tyr
                85                  90                  95

Arg Tyr Ile Leu Ser Cys His Cys Glu Glu Cys Asn Ser
            100                 105

<210> SEQ ID NO 3
<211> LENGTH: 133
<212> TYPE: PRT
<213> ORGANISM: Artificial sequence
<220> FEATURE:
<223> OTHER INFORMATION: Synthetic

<400> SEQUENCE: 3

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Glu
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
        130

<210> SEQ ID NO 4
<211> LENGTH: 133
<212> TYPE: PRT
<213> ORGANISM: Artificial sequence
```

<220> FEATURE:
<223> OTHER INFORMATION: Synthethic

<400> SEQUENCE: 4

Met Arg Lys His Val Leu Ala Ala Ser Phe Ser Met Leu Ser Leu Leu
1               5                   10                  15

Val Ile Met Gly Asp Thr Asp Ser Lys Ala Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 5
<211> LENGTH: 133
<212> TYPE: PRT
<213> ORGANISM: Artificial sequence
<220> FEATURE:
<223> OTHER INFORMATION: Synthetic

<400> SEQUENCE: 5

Met Arg Lys His Val Leu Ala Ala Ser Phe Ser Met Leu Ser Leu Leu
1               5                   10                  15

Val Ile Met Gly Asp Thr Asp Ser Lys Thr Asp Ala Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 6
<211> LENGTH: 133
<212> TYPE: PRT
<213> ORGANISM: Artificial sequence
<220> FEATURE:
<223> OTHER INFORMATION: Synthetic

<400> SEQUENCE: 6

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ala Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Arg Tyr Ile Leu Ser Cys His Cys
            115                 120                 125

Glu Glu Cys Asn Ser
    130

<210> SEQ ID NO 7
<211> LENGTH: 133
<212> TYPE: PRT
<213> ORGANISM: Artificial sequence
<220> FEATURE:
<223> OTHER INFORMATION: Synthetic

<400> SEQUENCE: 7

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Ala Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Arg Tyr Ile Leu Ser Cys His Cys
            115                 120                 125

Glu Glu Cys Asn Ser
    130

<210> SEQ ID NO 8
<211> LENGTH: 133
<212> TYPE: PRT
<213> ORGANISM: Artificial sequence
<220> FEATURE:
<223> OTHER INFORMATION: Synthetic

<400> SEQUENCE: 8

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

-continued

Asp Ser Asp Pro Ala Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
            130

<210> SEQ ID NO 9
<211> LENGTH: 133
<212> TYPE: PRT
<213> ORGANISM: Artificial sequence
<220> FEATURE:
<223> OTHER INFORMATION: Synthetic

<400> SEQUENCE: 9

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Ala Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
            130

<210> SEQ ID NO 10
<211> LENGTH: 133
<212> TYPE: PRT
<213> ORGANISM: Artificial sequence
<220> FEATURE:
<223> OTHER INFORMATION: Synthetic

<400> SEQUENCE: 10

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg

```
                    50                  55                  60
Cys Glu Gly His Cys Ser Gln Ala Ser Arg Ser Glu Pro Leu Val Ser
 65                  70                  75                  80

Phe Ser Thr Val Leu Lys Gln Pro Phe Arg Ser Ser Cys His Cys Cys
                 85                  90                  95

Arg Pro Gln Thr Ser Lys Leu Lys Ala Leu Arg Leu Arg Cys Ser Gly
                100                 105                 110

Gly Met Arg Leu Thr Ala Thr Ala Arg Tyr Ile Leu Ser Cys His Cys
                115                 120                 125

Glu Glu Cys Asn Ser
            130

<210> SEQ ID NO 11
<211> LENGTH: 133
<212> TYPE: PRT
<213> ORGANISM: Artificial sequence
<220> FEATURE:
<223> OTHER INFORMATION: Synthetic

<400> SEQUENCE: 11

Met Arg Lys His Val Leu Ala Ala Ser Phe Ser Met Leu Ser Leu Leu
  1               5                  10                  15

Val Ile Met Gly Asp Thr Asp Ser Lys Thr Asp Ser Ser Phe Ile Met
                 20                  25                  30

Asp Ser Asp Pro Arg Arg Cys Met Arg His His Tyr Val Asp Ser Ile
                 35                  40                  45

Ser His Pro Leu Tyr Lys Cys Ser Ser Lys Met Val Leu Leu Ala Arg
 50                  55                  60

Cys Glu Gly His Cys Ser Gln Ala Ser Arg Ser Glu Pro Leu Val Ser
 65                  70                  75                  80

Phe Ser Thr Val Leu Lys Gln Pro Phe Arg Ser Ser Cys His Cys Cys
                 85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Ala Tyr Ile Leu Ser Cys His Cys
                115                 120                 125

Glu Glu Cys Asn Ser
            130

<210> SEQ ID NO 12
<211> LENGTH: 133
<212> TYPE: PRT
<213> ORGANISM: Artificial sequence
<220> FEATURE:
<223> OTHER INFORMATION: Synthetic

<400> SEQUENCE: 12

Met Arg Lys His Val Leu Ala Ala Ser Phe Ser Met Leu Ser Leu Leu
  1               5                  10                  15

Val Ile Met Gly Asp Thr Asp Ser Lys Thr Asp Ser Ser Phe Ile Met
                 20                  25                  30

Asp Ser Asp Pro Arg Arg Cys Met Arg His His Tyr Val Asp Ser Ile
                 35                  40                  45

Ser His Pro Leu Tyr Lys Cys Ser Ser Lys Met Val Leu Leu Ala Arg
 50                  55                  60

Cys Glu Gly His Cys Ser Gln Ala Ser Arg Ser Glu Pro Leu Val Ser
 65                  70                  75                  80
```

```
Phe Ser Thr Val Leu Lys Gln Pro Phe Ser Ser Cys His Cys Cys
                85                  90                  95

Arg Pro Gln Thr Ser Lys Leu Lys Ala Leu Arg Leu Cys Ser Gly
            100                 105                 110

Gly Met Arg Leu Thr Ala Thr Tyr Arg Ala Ile Leu Ser Cys His Cys
        115                 120                 125

Glu Glu Cys Asn Ser
    130

<210> SEQ ID NO 13
<211> LENGTH: 133
<212> TYPE: PRT
<213> ORGANISM: Artificial sequence
<220> FEATURE:
<223> OTHER INFORMATION: Synthetic

<400> SEQUENCE: 13

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys Ala Cys
        115                 120                 125

Glu Glu Cys Asn Ser
    130

<210> SEQ ID NO 14
<211> LENGTH: 133
<212> TYPE: PRT
<213> ORGANISM: Artificial sequence
<220> FEATURE:
<223> OTHER INFORMATION: Synthetic

<400> SEQUENCE: 14

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110
```

Gly Met Arg Leu Thr Ala Thr Tyr Arg Tyr Ile Leu Ser Cys His Cys
            115                 120                 125

Ala Glu Cys Asn Ser
    130

<210> SEQ ID NO 15
<211> LENGTH: 133
<212> TYPE: PRT
<213> ORGANISM: Artificial sequence
<220> FEATURE:
<223> OTHER INFORMATION: Synthetic

<400> SEQUENCE: 15

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Ala Cys Asn Ser
    130

<210> SEQ ID NO 16
<211> LENGTH: 133
<212> TYPE: PRT
<213> ORGANISM: Artificial sequence
<220> FEATURE:
<223> OTHER INFORMATION: Synthetic

<400> SEQUENCE: 16

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Glu Gln Pro Phe Arg Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser

<210> SEQ ID NO 17
<211> LENGTH: 133
<212> TYPE: PRT
<213> ORGANISM: Artificial sequence
<220> FEATURE:
<223> OTHER INFORMATION: Synthetic

<400> SEQUENCE: 17

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Glu Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130
```

<210> SEQ ID NO 18
<211> LENGTH: 133
<212> TYPE: PRT
<213> ORGANISM: Artificial sequence
<220> FEATURE:
<223> OTHER INFORMATION: Synthetic

<400> SEQUENCE: 18

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Glu Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130
```

<210> SEQ ID NO 19
<211> LENGTH: 133

<212> TYPE: PRT
<213> ORGANISM: Artificial sequence
<220> FEATURE:
<223> OTHER INFORMATION: Synthetic

<400> SEQUENCE: 19

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Glu Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 20
<211> LENGTH: 133
<212> TYPE: PRT
<213> ORGANISM: Artificial sequence
<220> FEATURE:
<223> OTHER INFORMATION: Synthetic

<400> SEQUENCE: 20

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Glu Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 21
<211> LENGTH: 133
<212> TYPE: PRT
<213> ORGANISM: Artificial sequence
<220> FEATURE:
<223> OTHER INFORMATION: Synthetic

```
<400> SEQUENCE: 21

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
                20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Glu Leu Thr Ala Thr Tyr Arg Tyr Ile Leu Ser Cys His Cys
            115                 120                 125

Glu Glu Cys Asn Ser
    130
```